United States Patent
Liu et al.

(10) Patent No.: US 9,745,381 B2
(45) Date of Patent: Aug. 29, 2017

(54) BISPECIFIC SCFV IMMUNOFUSION (BIF)

(71) Applicant: Scott & White Healthcare, Temple, TX (US)

(72) Inventors: Jen-Sing Liu, Austin, TX (US); Shu-Ru Kuo, Temple, TX (US)

(73) Assignee: Scott & White Healthcare (SWH), Temple, TX (US)

( * ) Notice: Subject to any disclaimer, the term of this patent is extended or adjusted under 35 U.S.C. 154(b) by 110 days.

(21) Appl. No.: 14/402,009

(22) PCT Filed: May 18, 2013

(86) PCT No.: PCT/US2013/041739
§ 371 (c)(1),
(2) Date: Nov. 18, 2014

(87) PCT Pub. No.: WO2013/173820
PCT Pub. Date: Nov. 21, 2013

(65) Prior Publication Data
US 2015/0110789 A1  Apr. 23, 2015

Related U.S. Application Data

(60) Provisional application No. 61/649,211, filed on May 18, 2012.

(51) Int. Cl.
*C07K 16/28* (2006.01)
*C07K 16/30* (2006.01)

(52) U.S. Cl.
CPC .......... *C07K 16/30* (2013.01); *C07K 16/2809* (2013.01); *C07K 16/2896* (2013.01); *C07K 16/2866* (2013.01); *C07K 2317/31* (2013.01); *C07K 2317/52* (2013.01); *C07K 2317/56* (2013.01); *C07K 2317/622* (2013.01); *C07K 2317/64* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| 5,821,337 A | 10/1998 | Carter et al. | |
| 6,551,592 B2 * | 4/2003 | Lindhofer | C07K 16/2809 424/136.1 |
| 2007/0077246 A1 | 4/2007 | Koenig et al. | |
| 2012/0082670 A1 | 4/2012 | Konopitzky et al. | |

FOREIGN PATENT DOCUMENTS

| WO | WO 2009/017823 | 5/2009 |
| WO | WO 2011/034969 | 3/2011 |
| WO | WO 2012/065161 | 5/2012 |

OTHER PUBLICATIONS

Rudikoff et al (PNAS, 1982, vol. 79, pp. 1979-1983).*
Wang et al, Drug Metabolism and Disposition, 2011, vol. 39, pp. 1469-1477.*
Roopenian and Akilesh, Nature Reviews Immunology, 2007, vol. 7, pp. 715-725.*
Kiewe et al (Clinical Cancer Research, 2006, vol. 12, pp. 3085-3091).*
Stamova et al (Leukemia, 2011, vol. 25, pp. 1053-1056).*
Yalcintepe et al (Blood, 2006, vol. 108, pp. 3530-3537).*
Chichili et al., "A CD3xCD123 bispecific DART for redirecting host T cells to myelogenous leukemia: Preclinical activity and safety in nonhuman primates", *Science Translational Medicine*, 7(289): 289ra82-289ra82, 2015.
Chu et al., "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia", *Blood*, 124(21): 2316, 2014.
Extended European Search Report issued in European Application No. 13790217.7, dated on Mar. 21, 2016.
Henn et al., "Preclinical characterization of MT114, a novel CD33/CD3-bispecific BiTE antibody for the treatment of acute myeloid leukemia (AML)", *Cancer Research*, Apr. 15, 2012, XP055251939, Retrieved from the internet: URL:http://cancerres.aacrjournals.org/content/72/8_Supplement/3523 [retrieved on Feb. 22, 2016] *abstract*.
Kontermann, "Dual targeting strategies with bispecific antibodies", *mAbs*, 4(2): 182-197, 2012.
Kuo et al., "Engineering a CD123xCD3 bispecific scFv immunofusion for the treatment of leukemia and elimination of leukemia stem cells", *Protein Engineering*, 25(10): 561-569, 2012.
Moore et al., "A novel bispecific antibody format enables simultaneous bivalent and monovalent co-engagement of distinct target antigens", *mAbs*, 3(6): 546-557, 2011.
Mueller et al., "Bispecific Antibodies for Cancer Immunotherapy Current Perspectives", *Biodrugs*, 24(2): 89-98, 2010.
Pohl et al., "A Cassette Vector System for the Rapid Cloning and Production of Bispecific Tetravalent Antibodies", *Antibodies*, 1: 19-38, 2012.
Stein et al., "Novel conjugates of single-chain Fv antibody fragments specific for stem cell antigen CD123 mediate potent death of acute myeloid leukaemia cells", *British Journal of Haematology*, 148(6): 879-889, 2010.
Testa et al., "CD 123 is a membrane biomarker and a therapeutic target in hematologic malignancies", *Biomarker Research*, 2(1): p. 4, 2014.

* cited by examiner

*Primary Examiner* — Karen Canella
(74) *Attorney, Agent, or Firm* — Norton Rose Fulbright US LLP

(57) ABSTRACT

Certain embodiments are directed to a bispecific immunoglobulin that is capable of binding cell surface molecules on a target cell, such as cancer cells, and cell surface molecules on immune effector cell, such as cytotoxic T lymphocytes, resulting in the targeted killing of target cells. In certain aspects a Bif is a polypeptide comprising a first target binding domain that specifically binds a cancer cell, a second effector binding domain that specifically binds an immunologic effector, and an immunoglobulin constant region linker operatively coupling the first and second binding domain.

12 Claims, 9 Drawing Sheets

(A) CD123xCD3 BIf (B) UCHT1

(C) Flow Cytometry

BISPECIFIC SCFV IMMUNOFUSION (BIF)

This application is a U.S. National stage filing of International Application serial number PCT/US2013/041739 filed May 18, 2013, which claims priority to U.S. Provisional Patent Application Ser. No. 61/649,211 filed May 18, 2012 (expired). Priority to each of these applications is claimed and each application is incorporated herein by reference in its entirety.

First generation bispecific antibodies were developed over 20 years ago. Since then a number of clinical studies have tested bispecific antibodies engineered to target cancer cell surface antigens. This group of anti-cancer fusion proteins contains two or more functional domains that localize immunological effector cells in the proximity of targeted cancer cells to achieve anti-cancer activity.

One therapeutic agent of this family, Catumaxomab, was approved in 2009 by the European Union for the treatment of malignant ascites. Catumaxomab is a hybrid immunoglobulin of mouse and rat antibodies having a first binding site for EpCAM on tumor cell surface and a second binding site for CD3 of T lymphocytes. While the activated T cells provide the major cellular cytotoxicity, the Fc region through Fc receptors also bring macrophage, nature killer (NK) cells, and granulocytes to targeted cells activating the antibody-dependent cellular cytotoxicity (ADCC) responses. However, therapeutic antibodies carrying Fc of animal origins are typically immunogenic in humans and treated patients could adversely react to these therapeutic agents, reducing their half-life and efficacies. Murine antibodies are also associated with the generation of severe allergic reactions.

As bispecific antibody technology developed, a different group of fusion proteins named bispecific T-cell engagers (BiTE) were generated by connecting two antibody single chain variable regions (scFv) only (no Fc amino acid segments were included) with a flexible linker, one scFv binds targeted cells and the other binds CD3 on T cell surface. One BiTE, blinatumomab, with CD19×CD3 bi-specific binding activities showed promising results in Phase II clinical trials for patients with minimal residual disease in B-lineage acute lymphoblastic leukemia.

In spite of these advancements in bispecific antibody technology, there remains a need for additional cancer therapeutics, particularly those that efficiently target and kill cancer cells either directly or indirectly.

SUMMARY

Certain embodiments are directed to bispecific immunoglobulin therapeutics (bispecific scFV immunofusions, BIf) and methods of using such therapeutics. In certain aspects a BIf is a polypeptide comprising a first target binding domain that specifically binds a cancer cell, a second effector binding domain that specifically binds an immunologic effector, and an immunoglobulin constant region linker operatively coupling the first and second binding domain. As used herein the terms "specific binding" or "specifically binds" refers to a polypeptide domain that has a binding affinity predominately for a target cell type or protein and binds its target with a 10, 100, 1000 fold or greater affinity as compared to non-target cells or proteins.

In certain aspects, a target binding domain specifically binds to a cell surface polypeptide that is specifically expressed by a cancer cell or is over expressed by a cancer cell. In a further aspect, the cancer cell is a leukemia cell, including but not limited to acute myelogenous leukemia (AML), chronic myelogenous leukemia (CML), or plasmacytoid leukemia. In a further aspect the cancer cell can be, but is not limited to a colorectal, lung, breast, kidney, brain, prostate, pancreas, or blood cancer cell or a solid malignant tumor cell.

In certain aspects, the cell surface polypeptide is CD123. CD123 is also known as the interleukin-3 receptor (IL-3). IL-3 is a soluble cytokine that can be secreted by activated T cells. One example of CD123 binding domain comprises the variable regions of the anti-CD123 antibody 12F1 (amino acids 1 to 113, and 132 to 250 of SEQ ID NO:2). In certain aspects, the CD123 binding domain variable regions are, independently 80, 85, 90, 95, 98, or 100% identical to the variable regions of SEQ ID NO:2. In certain aspects, the CD123 binding domain is 80, 85, 90, 95, 98, or 100% identical to SEQ ID NO:2.

In further aspects, the cell surface polypeptide is tumor endothelial marker 8 ("TEM8") polypeptide. TEM8 is an 85 kDa integrin-like cell surface receptor that was originally identified as one of several unrelated genes (called TEM1-TEM9) overexpressed in vascular endothelial cells derived from tumor versus normal colorectal tissues. TEM8 is overexpressed in the blood vessels of a variety of human cancer types. One example of a TEM8 binding domain comprises the variable light chain region DIVMTQTPPS-VPVTPGESVSISCRSSKSLLHSNGNTYLYWFLQR-PGQSPQLLIYRMSNLASGVPDRFSGSGSGTAFTLRIS-RVEAEDVGVYYCMQHLEYPFTFGSGTKLEIKRA (SEQ ID NO:14) and/or the variable heavy chain region QVKLEESGAELVRPGVSVKISCKGSGYTFTDYAMH-WVKQSHAKSLEWIGVISTYFGDATYNQKFKGKAT-MTVDSSSTAYMELARLTSEDSAIYYCAREDYVPFAY-WGQGTLVTVSA (SEQ ID NO:15).

In still further aspects, the cell surface polypeptide is prostate-specific membrane antigen ("PSMA") polypeptide. PSMA (also known as Glutamate carboxypeptidase II) is a type 2 integral membrane glycoprotein found in prostate tissues and a few other tissues. One example of a PSMA binding domain comprises the variable light chain region WDIVMTQSHKFMSTSVGDRVSIICKASQDVGTAVD-WYQQKPGQSPKLLIYWASTRHTGVPDRFTGSGS-GTDFTLTITNVQSEDLADYFCQQYNSYPLTFGAGT-MLDLK (SEQ ID NO:16) and/or the variable heavy chain region EVQLQQSGPELKKPGTSVRISCKTSGYT-FTEYTIHWVKQSHGKSLEWIGNINPNNGGTTYN-QKFEDKATLTVDKSSSTAYMELRSLTSEDSAVYY-CAAGWNFDYWGQGTTLTVSS (SEQ ID NO:17).

In other embodiments, the cell surface polypeptide is a CD33 polypeptide. CD33 is a 67 kDa cell-surface antigen specifically expressed on myeloid cells including myeloid leukemia cells. It is the smallest member of the siglec (sialic acid-binding Ig-related lectins) family. One example of a CD33 binding comprises variable light chain region DIQLTQSPSSLSASVGDRVTITCRASQGISSVLAWY-QQKPGKAPKLLIYDASSLESGVPSRFSGSGSGTD-FTLTISSLQPEDFATYYCQQFNSSITFGQGTKLEIKR (SEQ ID NO:18) and/or variable chain region QVQLVQS-GAEVKKPGSSVKVSCKASGGTF-SDYAISWVRQAPGQGLEWMGRIIPILGVANYAQK-FQGRVTITADKSTRTAYMELSSLRSEDTAV YYCARNWADAFDIWGEGTMVTVSS (SEQ ID NO:19).

Certain aspects can include target binding domains that specifically bind cancer antigens that include, but are not limited to, MAGE (including but not limited to MAGE3, MAGEA6, MAGEA10), NY-ESO-1, gp100, tyrosinase, EGFR, PSA, VEG-F, PDGFR, KIT, CEA, HER2/neu, Muc-1, hTERT, MART1, TRP-1, and TRP-2.

In certain aspects, a BIf comprises a second effector-binding domain that binds an immunologic effector cell. In certain aspects the immunologic effector cell is a cytotoxic T lymphocyte. In certain aspects, the effector binding domain binds the CD3 protein. CD3 is a T-cell co-receptor that is composed of four distinct polypeptide chains. In mammals, the complex contains a CD3γ chain, a CD3δ chain, and two CD3ε chains. These chains associate with a molecule known as the T-cell receptor (TCR) and the ζ-chain to generate an activation signal in T-cells. In a further aspect, the effector binding domain comprises the variable regions of UCHT1 (amino acids 1 to 107 and 126 to 247 of SEQ ID NO:3). In certain aspects, the CD3 binding domain variable regions are independently 80, 85, 90, 95, 98, or 100% identical to the variable regions of SEQ ID NO:3. In certain aspects, the CD3 binding domain is 80, 85, 90, 95, 98, or 100% identical to SEQ ID NO:3.

In certain aspects, the variable regions of a binding domain are operatively linked by a peptide linker. In certain aspects, the target binding domain and the effector binding domain are operatively linked by a linker. The linker can be designed for optimal mammalian cell expression. In certain aspects the binding domains are linked using a hinge-$C_H2$-$C_H3$ domain or a hinge-$C_H3$ domain of human IgG1 constant region as a linker. In certain aspects, the IgG1 constant region is human. In certain aspects, the immunoglobulin constant region is 80, 85, 90, 95, 98, or 100% identical to SEQ ID NO:4.

Certain embodiments are directed to an immunofusion comprising a target binding domain operably linked by a hinge-$C_H2$-$C_H3$ domain or a hinge-$C_H3$ domain of an immunoglobulin constant region to an effector binding domain that specifically binds a CD3 expressing lymphocyte.

The term "operatively linked" or "operably linked" or the like, when used to describe fusion proteins, refer to polypeptide sequences that are placed in a physical and functional relationship to each other. In certain embodiments, the functions of the polypeptide components of the fusion molecule are unchanged compared to the functional activities of the parts in isolation.

In certain embodiments the first binding domain, linker, and second binding domain are comprised as a fusion protein. In certain aspects, the BIf is 80, 85, 90, 95, 98, or 100% identical to SEQ ID NO:1.

In certain aspects the nucleic acids encoding the binding domains and/or linker are codon optimized. In further aspects, the amino acid sequence of the binding domains and/or linker is human or humanized.

In certain embodiments, a cancer patient is treated for cancer by providing an effective amount of a BIf described herein. The term "providing" is used according to its ordinary meaning to indicate "to supply or furnish for use." In some embodiments, the protein is provided directly by administering the protein, while in other embodiments, the protein is effectively provided by administering a nucleic acid that encodes the protein.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains, Fab, Fab' F(ab')2, Fabc, and Fv. In certain embodiments the polypeptides are single chain Fv (scFV). In a further aspect the scFV can be further modified by a carboxy terminal fusion with a second antibody binding domain. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins. The term "antibody" also includes a bispecific antibody. A bispecific or bifunctional antibody is an artificial hybrid antibody having two different heavy/light chain pairs and two different binding sites.

The term "humanized antibody" refers to antibodies in which the framework and/or "complementarity determining regions" (CDR) are presented on an immunoglobulin of a different species as compared to that of the parent immunoglobulin from which the CDR was derived. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, et al. and Boerner, et al., are also available for the preparation of human monoclonal antibodies (Cole, et al., Monoclonal Antibodies and Cancer Therapy, Alan R. Liss, p. 77 (1985); and Boerner, P., et al., J. Immunol. 147 (1991) 86-95). The term "human antibody" as used herein also comprises such antibodies that are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (including the variable domain of a light chain (VL) and variable region of a heavy chain (VH)) as used herein denotes each of the pair of light and heavy chains that are involved directly in binding the antibody to the antigen. The domains of variable human light and heavy chains have the same general structure and each domain comprises four framework (FR) regions whose sequences are widely conserved and connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

The term "constant region" as used within the current applications denotes the sum of the domains of an antibody other than the variable region. The constant region is not involved directly in binding of an antigen, but exhibit various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

The phrase that a molecule "specifically binds" to a target refers to a binding reaction that is determinative of the presence of the molecule in the presence of a heterogeneous population of other biologics. Thus, under designated conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988), for a description of immunoassay formats and conditions that can be used to determine specific immunoreactivity. Specific binding between two entities means an affinity of at least $10^{-6}$, $10^{-7}$, $10^{-8}$, $10^{-9}$, $10^{-10}$ M, or greater.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figures 1A, 1B, 1C:
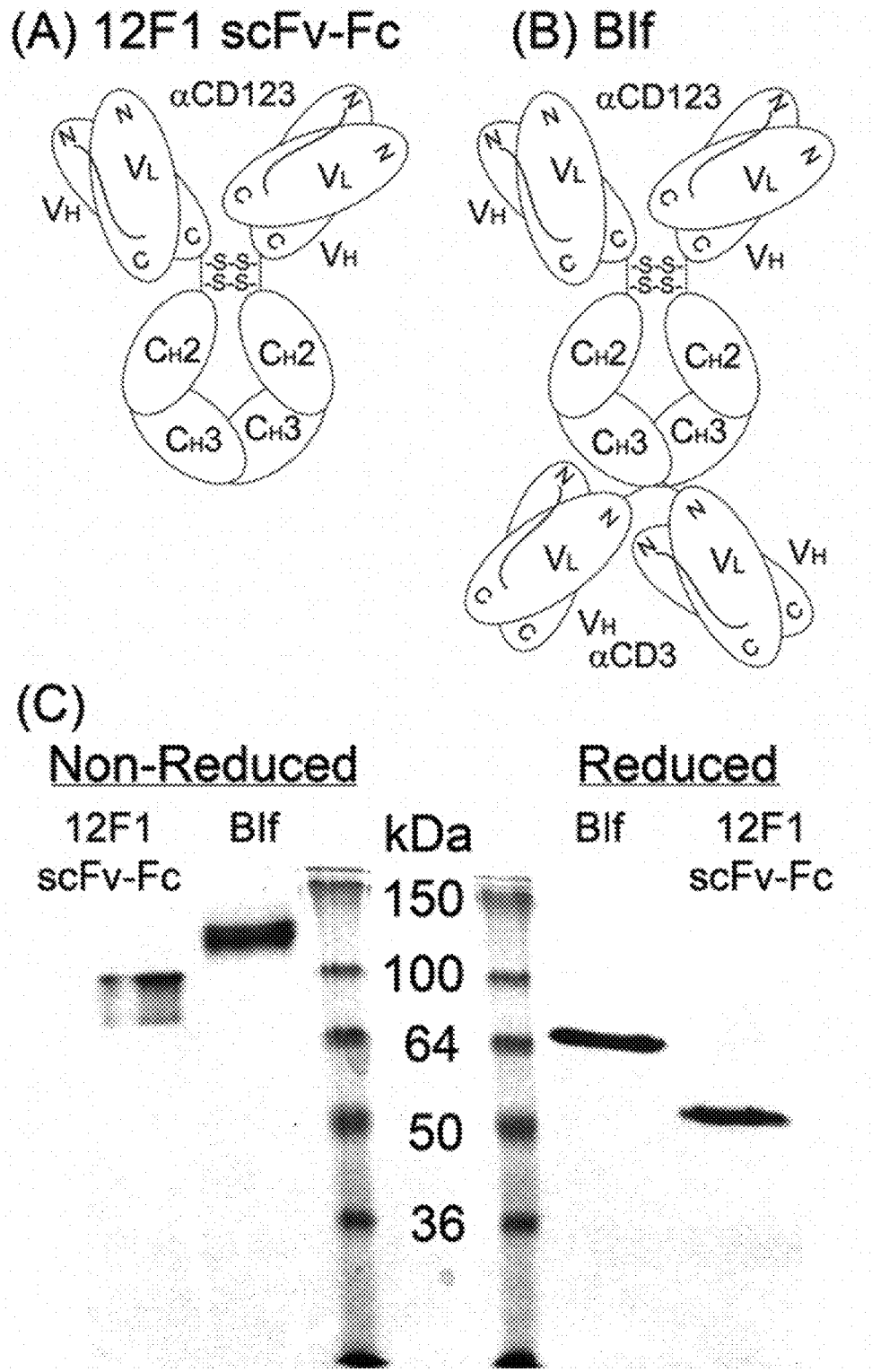
FIG. 1. 12F1scFv-Fc and CD123×CD3 BIf. Schematic diagram of 12F1scFv-Fc and CD123×CD3 BIf are shown in (A) and (B), respectively. (C) SDS-PAGE (12.5%) of purified 12F1scFv-Fc and CD123×CD3 BIf under reduced (right panel) and non-reduced (left panel) conditions.

A bispecific scFv immunofusion or BIf as described herein is capable of binding cell surface molecules on a target cell, such as cancer cells, and cell surface molecules on immune effector cell, such as cytotoxic T lymphocytes, resulting in the targeted killing of target cells at low effector to target ratio and/or drug doses.

In certain aspects, the BIf targets CD123+ leukemia. One example of a leukemia targeting BIf comprises an anti-CD123 single-chain Fv (scFv) domain fused at the N-terminus of human IgG1 hinge-$C_H2$-$C_H3$, and an anti-CD3 scFv fused at the C-terminus (CD123×CD3 BIf). In certain aspects, the human IgG1 Fc sequences can provide functional advantages. First, the Fc domain can form a dimer that provides a more natural antibody structure. The target cell binding affinity is between 10 to 100 fold higher than other monomeric scFv constructs. In certain aspects, the structural design can be a single polypeptide format that simplifies protein production. In a further aspect, the polypeptide can have a separate light chain and heavy chain having a chimeric antibody like structure. Second, the polypeptides can be bound by Fc receptors on NK cells, granulocytes and macrophage and engage ADCC functions. Unlike traditional bispecific antibodies, the human IgG1 Fc domain does not cause side effects associated with immunogenicity. Third, through the salvage system, Fc region plays a role in sustaining the antibody half-life in patient serum. Finally, the molecular weight of approximately 140 kDa can help to prevent kidney clearance. Thus, the polypeptides described herein have a longer serum half-life and better tumor targeting abilities.

Expression of the CD123×CD3 BIf in a host cell (e.g., CHO-S cells), results in a CD123×CD3 BIf homodimer. The BIf homodimer provides a structure of N-terminal tumor-targeting domain that closely resembles a natural antibody. The CD123×CD3 dimeric-structure also provides binding affinity to CD123+ tumor cells with a Kd of $10^{-10}$ M, which is 1 to 2 orders of magnitude stronger than traditional bispecific antibody constructs. The location of the anti-CD3 scFv at C-terminus of BIf reduces the binding affinity to $CD3^+$ T cells by 2 orders, which helps to prevent non-specific T cell activation. CD123×CD3 BIf is able to achieve T cell-mediated target cell killing activities at low pM levels with E/T ratios as low as 2. Overall, the inclusion of human IgG1 constant region in BIf construct increases target cell binding affinity and provides activation of additional antibody-mediated cellular cytotoxicities.

I. Leukemia Stem Cells

Certain embodiments are directed to targeting CD123+ cancer cells. An example of a CD123+ cell is the leukemia stem cell (LSC). LSCs are defined as a small population of leukemia blasts with $CD34^+/CD38^-$ cell surface markers that resemble hematopoietic stem cells (HSC) (Bonnet and Dick, 1997). LSC isolated from leukemia patients have the capacity to repopulate hematopoietic tissues with leukemia in NOD/SCID mice (Bonnet and Dick, 1997; Guan and Hoggs, 2000; Guzman et al, 2001; Hope et al, 2003; Hope et al, 2004; Lapidot et al, 1994; Wang and Dick, 2005), and possess multi-drug resistance to a variety of chemotherapeutic agents (Costello et al, 2000; Ishikawa et al, 2007). Clinically, poor survival has been attributed to high $CD34^+/CD38^-$ frequency at time of diagnosis in acute myeloid leukemia patients (van Rhenen et al, 2005). It is expected that therapeutic agents targeting LSC might be able to achieve durable remissions (Abutalib and Tallman, 2006; Aribi et al, 2006; Morgan and Reuter, 2006; Park et al, 2009; Stone, 2007).

The CD123 cell surface marker distinguishes LSC from hematopoietic stem cells (HSC) (Djokic et al, 2009; Florian et al, 2006; Graf et al, 2004; Hauswirth et al, 2007; Jordan et al, 2000; Munoz et al, 2001; Riccioni et al, 2004; Sperr et al, 2004; Testa et al, 2002; Yalcintepe et al, 2006). CD123 is the a subunit of interleukin-3 receptors (IL-3Rs). The function of interleukin-3 (IL-3) mediated through binding of IL-3Rs is to promote cell survival and proliferation (Bagley et al, 1997; Blalock et al, 1999; Miyajima et al, 1993; Yen and Yang-Yen, 2006), which is one major characteristic of cancer stem cells that make them more resistant to conventional chemotherapeutic agents. Therapeutic agents targeting CD123 or IL-3Rs would have the potential to eliminate the majority of LSC, and therefore, would have a better chance to achieve a longer disease-free survival in treated patients.

Two approaches have been used in Phase I AML clinical trials to target IL-3Rs. The first one is using a chimeric anti-CD123 antibody (CSL360) derived from mouse monoclonal antibody 7G3 (Jin et al, 2009; Sun et al, 1996). Animal studies with leukemia mouse model showed that 7G3 effectively eliminates AML-LSC through blocking the homing effect of LSC as well as the activation of antibody-dependent cellular cytotoxicity (ADCC) (Jin et al, 2009). While the administration of CSL360 is safe for patients, the early Phase I data showed minimal efficacy (Roberts et al, 2010). The other Phase I trial is an immunotoxin, $DT_{388}IL3$ (Liu et al, 2010). $DT_{388}IL3$ is a fusion protein consisting of the catalytic and translocation domains of diphtheria toxin ($DT_{388}$) fused to human IL-3 (Frankel et al, 2008; Frankel et al, 2000; Urieto et al, 2004). Binding of IL-3 to IL-3Rs leads to cellular internalization of $DT_{388}IL3$ and results in the activation of apoptosis and cell death (Sandvig and van Deurs, 2002; Thorburn et al, 2004). $DT_{388}IL3$ was found to be specifically cytotoxic toward AML cell lines and AML-LSC, but not HSC (Feuring-Buske et al, 2002). $DT_{388}IL3$ has been tested in patients with refractory or relapsed AML or high-risk myelodysplastic syndrome, and at current dose levels, no irreversible liver or kidney toxicity was observed. There were 2 cases of complete remissions and several partial remissions (Liu et al, 2010). Although the response rate to $DT_{388}IL3$ is low, the results did provide the proof of principle that targeting IL-3Rs is relatively safe and could have impact on AML treatment.

Donor lymphocyte infusion has been utilized for hematological malignancies after allogeneic stem cell transplantation (Kolb et al, 2009; Ringden et al, 2009). The graft-versus-leukemia activity after lymphocyte infusion has been shown to produce durable remissions. However, these clinical responses were only observed in a limited number of patients (Oliansky et al, 2008). In addition, serious complications from the graft-versus-host disease have the potential to induce morbidity and mortality during therapy (Biagi et al, 2007). Collectively, these clinical findings have fueled translational research for novel therapeutic approaches to enhance the clinical benefits of lymphocyte infusion therapy while minimizing the potential for unwanted side effects.

Certain polypeptides described herein can be used as a therapeutic agent to target CD123+ leukemia blasts and LSC, e.g., CD123×CD3 polypeptide. These novel fusion proteins belong to a family of bispecific antibodies (Kontermann 2012; Choi et al, 2011). The 12F1 anti-CD123 murine monoclonal antibody, the highest binding affinity obtained by Kuo et al (2009) was chosen to be used in BIf construction. Single-chain anti-CD3 antibody was derived from UCHT1 (Woo et al, 2008; Thompson et al, 2001; Hexham et al., 2001) with optimized codon usage and linker design for mammalian cell expression. Different from BiTE, these two scFvs were bridged with a hinge-$C_H2$-$C_H3$ domain of human IgG1 constant region. A similar type of construct was described before (Croasdale et al., 2012; Dong et al, 2011; Coloma and Morrison, 1997) that carries a natural heavy/light-chain tetrameric structure, but with an additional scFv to a secondary antigen fused to the heavy chain C-terminus. When expressed and secreted from a single plasmid in suspension cultured CHO-S cells, the BIf fusion protein forms a homo-dimer. The N- and C-terminal pairs of scFv sites with Y-shaped binding orientations share the same Fc region as the vertical stem. Each scFv was able to bind specific cell surface antigen and brought cytotoxic T lymphocytes to kill targeted cells at low effector to target ratio and drug doses.

The inclusion of human IgG1 Fc sequences in a bispecific immunoglobulin served several functional advantages. First, the Fc domain forms dimer that provides a more natural antibody structure to tumor cell targeting domain. The data showed the target cell binding affinity of CD123×CD3 BIf is about 5 times lower than the parental antibody 12F1, but this tumor cell targeting activity is 1-2 orders of magnitude higher than other monomeric scFv constructs (Stein et al, 2010; Hammond et al, 2007; Buhler et al, 2008; Moore et al, 2011). Due to its natural antibody-like structure, further humanization of CD123×CD3 to reduce immunogenicity is possible. Second, CD123×CD3 has the potential to be bound by Fc receptors on NK cells, granulocytes and macrophage and engage ADCC functions (Croasdale et al., 2012). But unlike catumaxomab, the human IgG1 Fc domain will not cause the side effects associated with immunogenicity. Third, through FcRn-mediated salvage system, human IgG1 Fc region could play a role in sustaining the antibody half-life in patient serum. Besides, compared to BiTE at 50 kDa, CD123×CD3 has a molecular weight at 140 kDa that would also help to prevent kidney clearance. Together, it is contemplated that CD123×CD3 will have a longer serum half life and better tumor targeting abilities.

There is a CD123×CD16 bispecific antibody reported that recruits NK cells for tumor cell killing (Kugler et al, 2010; Stein et al, 2010). Compared to CSL360, CD123×CD16 brought additional CD123+ cell killing activities. However, when PBMC was used in their studies, the required E/T ratio was above 20. The inventors choose to engage cytotoxic T cells for their high cytotoxic potential, abundance, and ability to penetrate solid tumors. Besides, cytotoxic T lymphocytes have a proven track record for their potential to destroy malignant diseases in patients.

II. Polypeptide Compositions

Compositions of the invention include various BIfs as described above. As used herein, an amino acid sequence or a nucleotide sequence is "substantially the same as" or "substantially similar to" a reference sequence if the amino acid sequence or nucleotide sequence has at least 85% sequence identity with the reference sequence over a given comparison window. Thus, substantially similar sequences include those having, for example, at least 85% sequence identity, at least 90% sequence identity, at least 95% sequence identity or at least 99% sequence identity. Two sequences that are identical to each other are also substantially similar.

Sequence identity is calculated based on a reference sequence. Algorithms for sequence analysis are known in the art, such as BLAST, described in Altschul et al., J. Mol. Biol., 215, pp. 403-10 (1990). In one aspect, comparisons of nucleic acid or amino acid sequences are performed with Blast software provided by the National Center for Biotechnology Information using a gapped alignment with default parameters, may be used to determine the level of identity and similarity between nucleic acid sequences and amino acid sequences.

Mutants or variants may retain biological properties of the bispecific immunoglobulin (SEQ ID NO:1, 2, 3, and/or 4). Mutations or substitutions include single amino acid changes, deletions or insertions of one or more amino acids, N-terminal truncations or extensions, C-terminal truncations or extensions and the like. Each polypeptide component of the bispecific immunoglobulin can be varied in such a way as to produce a variant or mutant of the protein defined in SEQ ID NO:1, 2, 3, and/or 4.

Mutants or variants can be generated using standard techniques of molecular biology as described in detail in the section "Nucleic Acid Molecules." Given the guidance provided in the Examples, and using standard techniques, those skilled in the art can readily generate a wide variety of additional mutants and test whether a biological property has been altered. For example, binding affinities or killing efficiency can be measured using in vitro assays.

The proteins of the subject invention are present in a non-naturally occurring environment, e.g., are recombinant or engineered proteins. The proteins of the present invention may be present in the isolated form, by which is meant that the protein is substantially free of other proteins and other naturally-occurring biological molecules, such as oligosaccharides, nucleic acids and fragments thereof, and the like, where the term "substantially free" in this instance means that less than 70%, usually less than 60% and more usually less than 50% of the composition containing the isolated protein is some other natural occurring biological molecule. In certain embodiments, the proteins are present in substantially purified form, where by "substantially purified form" means at least 95%, usually at least 97% and more usually at least 99% pure. In other aspects, the proteins described herein can be expressed in vitro or in vivo, including expression in transgenic cells or transgenic model animals.

The subject proteins may be synthetically produced, e.g., by expressing a recombinant nucleic acid coding sequence encoding the protein of interest in a suitable host, as described above. Any convenient protein purification procedures may be employed, wherein suitable protein purification methodologies are described in Guide to Protein Purification, (Deuthser ed., Academic Press, 1990). For example, a lysate may be prepared from the original source and purified using HPLC, exclusion chromatography, gel electrophoresis, affinity chromatography, and the like.

III. Nucleic Acid Molecules

The present invention provides nucleic acid molecules encoding a BIf as described herein. In one embodiment the BIf has an amino acid sequence of SEQ ID NO:1 and can include various mutants or variants thereof. Nucleic acid molecules encoding shorter or longer variants of the BIf or its variants are also in the scope of the invention.

A nucleic acid molecule as used herein is a DNA molecule, such as a cDNA molecule, or an RNA molecule, such as an mRNA molecule. The term "cDNA" as used herein is intended to include nucleic acids that share the arrangement of sequence elements found in mature mRNA species, where sequence elements are exons and 5' and 3' non-coding regions.

Nucleic acid molecules encoding the BIf of the invention may be synthesized from appropriate nucleotide triphosphates or isolated from recombinant biological sources. Both methods utilize protocols well known in the art. For example, the availability of amino acid sequence information provided herein enables preparation of isolated nucleic acid molecules of the invention by oligonucleotide synthesis or by recombinant techniques. In the case of amino acid sequence information, a number of nucleic acids that differ from each other due to degenerate code may be synthesized. The methods to select codon usage variants for desired hosts, such as humans, are well known in the art.

Synthetic oligonucleotides may be prepared by the phosphoramidite method, and the resultant constructs may be purified according to methods known in the art, such as high performance liquid chromatography (HPLC) or other methods as described in, for example, Sambrook et al., Molecular Cloning: A Laboratory Manual, 2nd Ed., (1989) Cold Spring Harbor Press, Cold Spring Harbor, N.Y., and under regulations described in, e.g., United States Dept. of HHS, National Institute of Health (NIH) Guidelines for Recombinant DNA Research. Long, double-stranded DNA molecules of the present invention may be synthesized by synthesizing several smaller segments of appropriate complementarity that comprise appropriate cohesive termini for attachment of an adjacent segment. Adjacent segments may be linked using DNA ligase or PCR-based methods.

Nucleic acid molecules encoding the domains and/or linkers described herein or their equivalent may be also cloned from biological sources or known recombinant nucleic acids.

In certain embodiments, a nucleic acid molecule of the invention is a DNA (or cDNA) molecule comprising an open reading frame that encodes the bispecific immunoglobulins described herein and is capable, under appropriate conditions (e.g., cell physiological conditions), of being expressed as a bispecific immunoglobulin according to the invention. The invention also encompasses nucleic acids that are homologous, substantially the same as, identical to, or variants of the nucleic acids encoding proteins described herein. The subject nucleic acids are recombinant nucleic acids, i.e., they are engineered nucleic acids not present in nature.

A nucleic acid encoding a BIf polypeptide which is an amino acid sequence variant of the sequence shown in SEQ ID NO:1 is further provided by the present invention. A nucleic acid encoding such polypeptide may show greater than 60, 70, 80, 90, 95, or 99% identity with a nucleic acid encoding SEQ ID NO: 1.

Variant nucleic acids can be generated on a template nucleic acid selected from the described-above nucleic acids by modifying, deleting, or adding one or more nucleotides in the template sequence, or a combination thereof, to generate a variant of the template nucleic acid. The modifications, additions or deletions can be introduced by any method known in the art (see for example Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108) including error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-directed mutagenesis, random mutagenesis, gene reassembly, gene site saturated mutagenesis (GSSM), synthetic ligation reassembly (SLR), or a combination thereof. The modifications, additions or deletions may be also introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In addition, degenerate variants of the nucleic acids that encode the proteins of the present invention are also provided. Degenerate variants of nucleic acids comprise replacements of the codons of the nucleic acid with other codons encoding the same amino acids. In particular, degenerate variants of the nucleic acids are generated to increase its expression in a host cell. In this embodiment, codons of the nucleic acid that are non-preferred or less preferred in genes in the host cell are replaced with the codons overrepresented in coding sequences in genes in the host cell, wherein said replaced codons encode the same amino acid. Humanized versions of the nucleic acids of the present invention are of particular interest. As used herein, the term "humanized" refers to changes made to the nucleic acid sequence to optimize the codons for expression of the protein in mammalian (human) cells (Yang et al., Nucleic Acids Research (1996) 24: 4592-4593). See also U.S. Pat. No. 5,795,737, which describes humanization of proteins, the disclosure of which is herein incorporated by reference.

Also provided are vector and other nucleic acid constructs comprising the subject nucleic acids. Suitable vectors include viral and non-viral vectors, plasmids, cosmids, phages, etc., preferably plasmids, and used for cloning, amplifying, expressing, transferring etc. of the nucleic acid sequence of the present invention in the appropriate host. The choice of appropriate vector is well within the skill of the art, and many such vectors are available commercially. To prepare the constructs, the partial or full-length nucleic acid is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems used inter alia for the production of the subject bispecific immunoglobulin or for replication of the subject nucleic acid molecules. The expression cassette may exist as an extra-chromosomal element or may be integrated into the genome of the cell as a result of introduction of said expression cassette into the cell. For expression, the gene product encoded by the nucleic acid of the invention is expressed in any convenient expression system, including, for example, bacterial, yeast, insect, amphibian, or mammalian systems. In the expression vector, a subject nucleic acid is operatively linked to a regulatory sequence that can include promoters, enhancers, terminators, operators, repressors and inducers. Methods for preparing expression cassettes or systems capable of expressing the desired product are known for a person skilled in the art.

Cell lines, which stably express the proteins of present invention, can be selected by the methods known in the art (e.g., co-transfection with a selectable marker such as dhfr, gpt, neomycin, hygromycin allows the identification and isolation of the transfected cells that contain the gene integrated into a genome).

The above-described expression systems may be used in prokaryotic or eukaryotic hosts. Host-cells such as *E. coli, B. subtilis, S. cerevisiae*, insect cells in combination with baculovirus vectors, or cells of a higher organism such as vertebrates, e.g., COS 7 cells, HEK 293, CHO, *Xenopus* oocytes, primary cells etc., may be used for production or expression of the protein.

When any of the above-referenced host cells, or other appropriate host cells or organisms are used to replicate and/or express the nucleic acids of the invention, the resulting replicated nucleic acid, expressed protein or polypeptide is within the scope of the invention as a product of the host cell or organism. The product may be recovered by an appropriate means known in the art.

IV. Pharmaceutical Compositions And Administration Thereof

One aspect of the invention is a pharmaceutical composition comprising a BIf as described herein. Another aspect of the invention is the use of bispecific antibody for the manufacture of a pharmaceutical composition. A further aspect of the invention is a method for the manufacture of a pharmaceutical composition comprising a bispecific immunoglobulin as described herein. In another aspect, the present invention provides a composition, e.g. a pharmaceutical composition, containing a bispecific immunoglobulin as described herein, formulated together with a pharmaceutical carrier.

One embodiment of the invention is a bispecific immunoglobulin as described herein for the treatment of cancer. Another embodiment is directed to pretreating blood transfusion or transplant products, tissues, or organs to reduce the number of CD123+ cells in the transfusion or transplant candidate.

Another aspect of the invention is said pharmaceutical composition for the treatment of cancer.

Another aspect of the invention is the use of a bispecific immunoglobulin as described herein for the manufacture of a medicament for the treatment of cancer.

Another aspect of the invention is method of treatment of patient suffering from cancer by administering a bispecific immunoglobulin as described herein to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as leukemias and any other cancer in which CD123+ cancer cells can be detected, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

V. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

CD123×CD3 Bispecific Immunoglobulins

A. Materials and Methods

Cell Lines and Antibodies. Jurkat, TF1/H-ras (Kiser et al, 2001) and U-937 cells were maintained in RPMI medium containing 10% FBS. CHO-K1 cells (ATCC) were maintained in ATCC-formulated F-12K medium containing 10% FBS. Human CD123 stably transfected CHO-K1 (CHO-CD123) cells were maintained in F-12K medium supplemented with 10% FBS and 0.4 mg/ml zeocin (Invitrogen). FreeStyle CHO-S cells (Life Technologies/Invitrogen) were maintained in FreeStyle CHO Expressing medium supplemented with 8 mM L-glutamine. Hybridoma cells producing murine anti-human CD123 antibody 12F1 was described previously (Kuo et al, 2009).

Construction of 12F1scFv-Fc and CD123×CD3 BIf Expressing Plasmids. Complementary DNA of 12F1 variable regions were amplified by RT-PCR using total RNA extraction RNeasy kit (Qiagen), One-step RT-PCR kit (Qiagen) and mouse Ig-primer sets (EMD Bioscience). Amplified DNA fragments were cloned into linear pDrive TA cloning vector (Qiagen) and the PCR inserts were sequenced. Correct light chain variable ($V_L$) and heavy chain variable ($V_H$) sequences were verified by comparing with mouse immunoglobulin sequences database (AntibodyResource.com). The 12F1 scFv, in the order of $V_L$-218L-$V_H$, was subsequently created by overlapping PCR amplification of $V_L$ and $V_H$ using the following primer pairs: P1 (GATATCGGACATTATGATGTCACAG)(SEQ ID NO:5) and P2 (TTCACCGCTTCCCGGTTTTCCGGAGC-CAGAGGTGCTACCTTTGATTTCCAGTTTGGT)(SEQ ID NO:6); and P3 (TCCGGAAAACCGGGAAGCGGT-GAAGGGTCCACCAAGGGTGTGCAGCTTCAG-GAGTCG)(SEQ ID NO:7) and P4 (AGATCTGGCTGAG-GAGACTGTGAGAGT)(SEQ ID NO:8), respectively. Primers P2 and P3 have a 24 base-pair complementary overlap and each encoded an 18 residue 218L linker (GST- SGSGKPGSGEGSTKG)(SEQ ID NO:9) (Whitlow et al, 1993; Vallera et al, 2009). The 12F1scFv was then cloned into EcoRV and BglII sites of pINFUSE-hIgG1-Fc2 vector (InvivoGen) to generate 12F1scFv-Fc expression plasmid p12F1scFv-hIg. Codon optimized single-chain anti-CD3 antibody sequence was derived from murine mAb UCHT1 with an upstream linker sequence (AGATCTGGATCAC-CATGG)(SEQ ID NO:10), followed by $V_L$, 218L linker, $V_H$ and a downstream termination codon & linker sequences (TAACTCGAGGCTAGC)(SEQ ID NO:11). DNA was synthesized by GenScript (Piscataway, N.J.) and cloned into the BglII and NheI sites of p12F1scFv-hIg to generate p12F1scFv-scUCHT1. Human IgG1 hinge-$C_H2$-$C_H3$ fragment was obtained by PCR with primers P5 (AGATCT-GACAAAACTCACACATGC)(SEQ ID NO:12) and P6 (CCATGGTTTACCCGGAGACAGGGA)(SEQ ID NO:13) and cloned into BglII and NcoI sites of psc12F1-scUCHT1 to generate CD123×CD3 BIf expressing plasmid, pCD123× CD3BIf. From 5'- to 3'-ends, the coding region sequence is: $V_L$(12F1)-218L-$V_H$(12F1)-hinge-$C_H2$-$C_H3$-$V_L$(UCHT1)-218L-$V_H$(UCHT1).

Expression and Purification of 12F1scFv-Fc and CD123× CD3 BIf. Secreted 12F1scFv-Fc or CD123×CD3 BIf were expressed in CHO-S cells transiently transfected with plasmids p12F1scFv-hIg or pCD123×CD3BIf using TransIT-PRO transfection reagents (Mirus). Culture supernatant was harvested 6 days post-transfection and mixed with 0.5 ml of Protein G Sepharose beads (GE Healthcare) at 4° C. for 16-18 hours. Proteins were eluted with 100 mM triethylamine pH 11.0 and neutralized immediately with 1/10 volume of 1M sodium phosphate pH 6.0. PD-10 desalting column (GE Healthcare) was used to exchange the buffer of purified protein to phosphate buffer saline (PBS) pH 7.4. Proteins were sterilized through 0.2 µm syringe filter (PALL). Protein concentrations were measured by Bradford assays (Bio-Rad) with BSA (Pierce) as standards and verified by reduced 12.5% SDS polyacrylamide gel electrophoresis under reduced or non-reduced condition, and coomassive blue R-250 staining. The protein yield is 2-5 mg/L.

Flow Cytometric Analysis. Log phase growing monolayer cells were harvested with trypsin/EDTA solution (ATCC) and washed once with culture media and once with PBS containing 1% BSA. $1 \times 10^6$ cells were resuspended in 200 µl staining solution (PBS, 1% BSA, 3% normal goat serum and indicated concentration of 12F1, 12F1scFv-Fc or CD123× CD3 BIf) at room temperature for 1 hour. Human IgG1 (Sigma) was used as a control. Cells were rinsed twice with PBS containing 1% BSA and incubated with PE-conjugated goat anti-human or anti-mouse antibody (Jackson Lab) at room temperature for 1 hour. Cells were thrice washed with PBS containing 1% BSA, resuspended in 500 µl of PBS and analyzed on a Beckman Coulter Cytomic FC 500 flow cytometry.

Cell-Based Enzyme-Linked Immunosorbent Assay (CELISA). One day prior to the experiment, $5 \times 10^4$ CHO-K1 or CHO-CD123 cells were seeded in each well of a flat-bottom 96-well plate. The next day, cells were washed with PBS and fixed with 3% formaldehyde in PBS at room temperature for 10 minutes. Fixed cells were washed thrice with PBS containing 0.5% Tween-20 (PBST) and incubated in Blocking Solution (PBS with 10% goat serum) for 30 minutes. A titration of 12F1, 12F1scFv-Fc or CD123×CD3 BIf was then added at room temperature for 60 minutes, followed by washing with PBST and then 45 minutes incubation with HRP-conjugated anti-mouse or anti-human secondary antibodies (Jackson Lab) at room temperature. The HRP activity was detected by HRP substrate (R&D) for 10 minutes and stopped by 0.5N $H_2SO_4$. The plates were read by a plate reader set at 450 nm.

Determination of Binding Affinities. For antigen on monolayer cultured cells (CHO-CD123), cell-based enzyme-linked immunosorbent assay (CELISA, see above) was used to evaluate binding affinities (Kuo et al, 2009). The fusion protein or antibody concentration that has 50% of maximal binding capacities was defined as Kd. For suspension cultured cells, flow cytometry was used to measure binding affinities. The fusion protein or antibody concentrations that achieve the X-axis mean value at 50% of maximal mean value was defined as Kd.

CFSE Labeled Target Cells. CHO-K1 and CHO-CD123 cells were harvested and washed twice with PBS and resuspended in 1 ml of PBS. Two µl of freshly prepared CellTrace (Invitrogen) CFSE (5 mM in DMSO) were added into cell suspension and incubate at 37° C. for 15 minutes. Labeled cells were washed twice with PBS, resuspended in culture medium and seeded in black 96-well glass-bottom plate (Costar) at $4 \times 10^4$ cell/well for cellular cytotoxicity assays.

Isolation of Peripheral Blood Lymphocytes and T Lymphocytes. Human peripheral blood mononuclear cells (PBMCs) were isolated from fresh buffy coats of consented healthy donors using Ficoll-Paque Premium gradient centrifugation solution (GE Healthcare) or purchased from Astarte Biologics (Redmond, Wash.). After overnight incubation at 37° C., 5% $CO_2$ in RPMI medium containing 10% heat-inactivated FBS and 100 units/ml of recombinant human IL-2 (eBioscience), the nonadherent fraction of PBMCs was collected and used as peripheral blood lymphocytes (PBL).

Human T lymphocytes were enriched from fresh blood of consented donors using RosetteSep HLA enrichment cocktail (StemCell Technologies) and cultured at 37° C., 5% $CO_2$ in RPMI medium containing 10% heat-inactivated FBS and 100 units/ml of recombinant human IL-2.

Cellular Cytotoxicity Assays. Cytotoxicity was measured in a standard colorimetrric quantitative lactate dehydrogenase (LDH) release measurement assay (Promega) following manufactural instruction. Briefly, $4 \times 10^4$ target cells were mixed with different amounts of 12F1scFv-Fc or CD123× CD3 BIf and T lympnocyte fraction at indicated effector to target (E/T) ratio. Cells were incubated at 37° C. and 5% $CO_2$ for 18-24 hours. After centrifugation, 50 µl of clear supernatant from each well was withdrawn, transferred to another 96-well plate and mixed with 50 µl of LDH assay substrate at room temperature for 30 minutes. LDH activities released from the same number of target cells treated with Triton Lysis Solution, after subtracting the targeted cell spontaneous LDH release, was defined as 100% lysis activity.

For CHO-K1 and CHO-CD123 cells, toxicity assays were also tested in CFSE-labeled target cells. Labeled cells were seeded in black 96-well plates with glass bottoms for 4-6 hours to ensure proper attachment. Fusion proteins and effector cells were added at indicated amounts and incubated at 37° C. and 5% $CO_2$ for 18-24 hours. Cells were washed twice with PBS. CFSE fluorescent counts in remaining cells were measured with a GloMax fluorescent plate reader (Promega). The fluorescence reading of mock-treated target cells were defined as 100%. Images were also taken by fluorescent microscope and labeled by Adobe Photoshop.

B. Results

Construction of 12F1scFv-Fc and CD123×CD3 BIf. Predicted protein structures of 12F1scFv-Fc and CD123×CD3 BIf were shown in FIGS. 1A and 1B. The only difference between these two fusion proteins is that BIf carries the additional C-terminal single-chain anti-CD3 antibody sequences. When transiently expressed from CHO-S cells, 12F1scFv-Fc had a higher yield at 5 mg/L versus CD123×CD3 BIf at 2 mg/L. Single step Protein G Sepharose purification yields high purities of both fusion proteins (FIG. 1C).

Figures 2A, 2B, 2C, 2D:
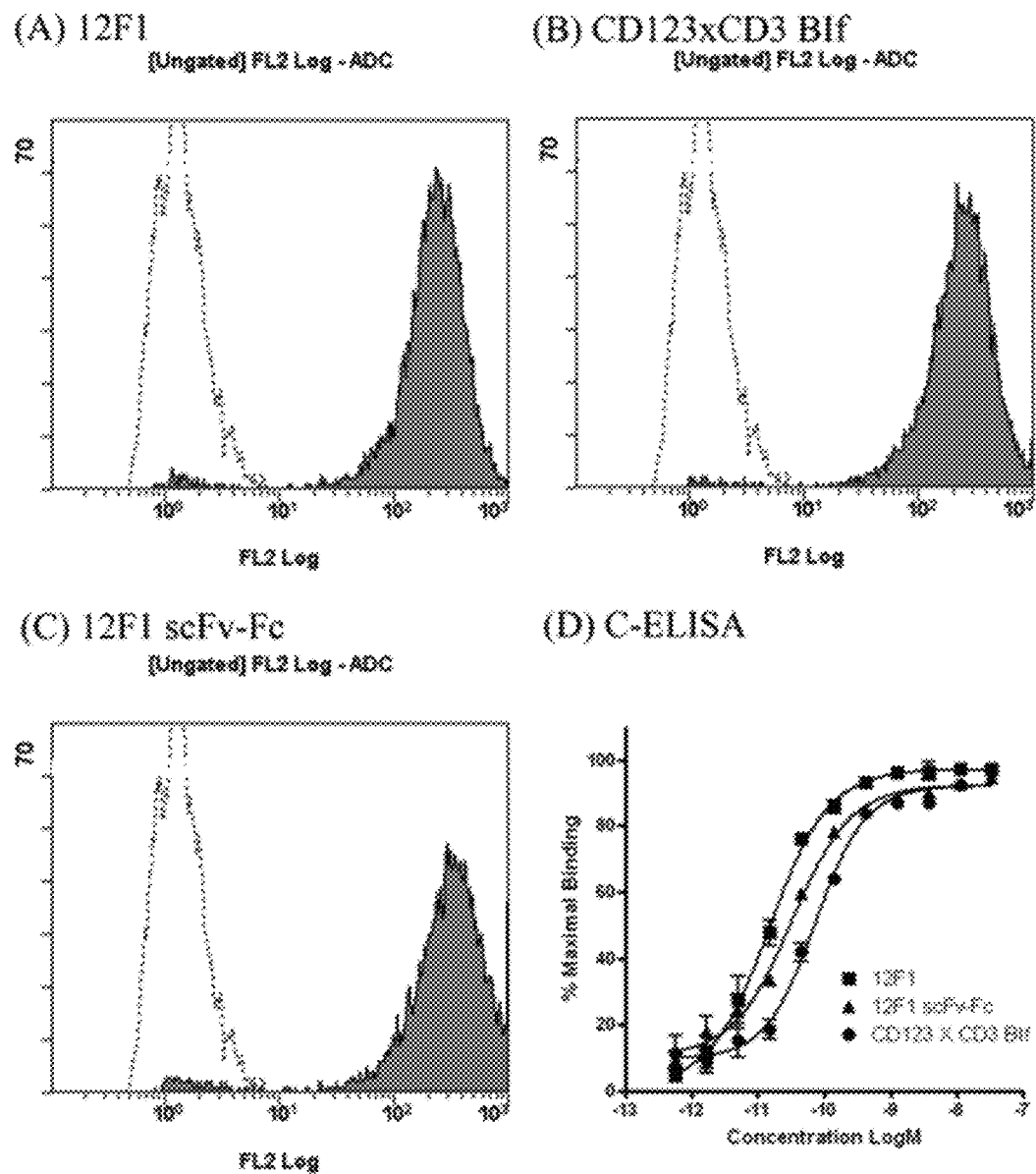
FIG. 2. Cell surface binding of 12F1scFv-Fc and CD123×CD3 BIf. Binding of 1 µg/ml of (A) 12F1; (B) CD123×CD3 BIf and (C) 12F1scFv-Fc to CHO-CD123 was analyzed by flow cytometry with PE-conjugated secondary antibodies. The dotted histogram represented the reaction with human IgG1 control. The y-axis represented cell counts. (D) 96-well plate coated with $5 \times 10^4$ CHO-CD123 cells/well was fixed and probed by serial titrations of 12F1 (square); 12F1scFv-Fc (triangle); and CD123×CD3 BIf (circle) and detected with HRP-conjugated goat-anti-mouse (12F1) or goat-anti-human (12F1scFv-Fc and CD123×CD3 BIf) antibodies. The average of three sets of reactions was plotted by GraphicPad Prism.

Cell Surface CD123 Binding Activities. The abilities of 12F1scFv-Fc and CD123×CD3 BIf to bind cell surface CD123 were examined by flow cytometry using CHO-K1 and CHO-CD123. 12F1 murine monoclonal antibody was used as a positive control. At 1 µg/ml, all three proteins showed strong binding activities to CHO-CD123 cells (FIGS. 2A to 2C), but not CHO-K1 cells (data not shown). The binding affinities were tested in cell-based ELISA with CHO-CD123 cells. The 12F1scFv-Fc and CD123×CD3 BIf showed lower binding affinities than 12F1 (FIG. 2D), but the Kd values are still at between $10^{-11}$ and $10^{-10}$M, a target-cell affinity that is 1-2 orders higher than any currently developed bispecific antibodies with monomeric scFv (Stein et al, 2010; Hammond et al, 2007; Buhler et al, 2008; Moore et al, 2011).

Figure 3A:
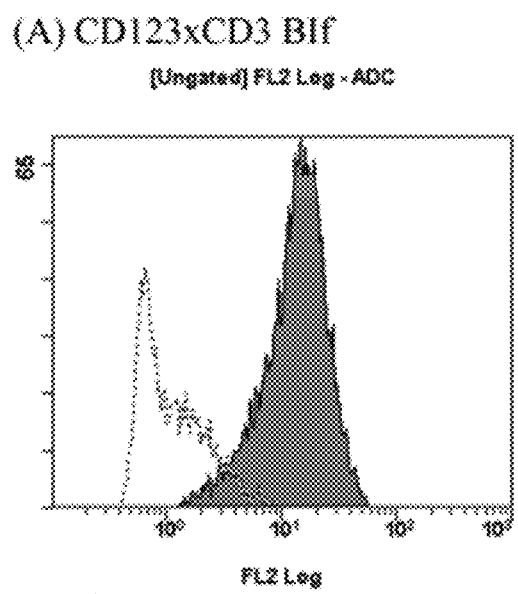
FIG. 3. T-cell surface binding of CD123×CD3 BIf. Binding of 1 µg/ml of (A) CD123×CD3 BIf; and (B) UCHT1 to Jurkat T cells was analyzed by flow cytometry with PE-conjugated secondary antibodies. The dotted histogram represented the reaction with human IgG1 control. The y-axis represented cell counts. (C) Serials titrations of UCHT1 (square) and CD123×CD3 BIf (triangle) were used in flow cytometric analysis with Jurkat T cells. The mean X-axis values were plotted versus protein concentrations for Kd analysis.
Figure 3B:
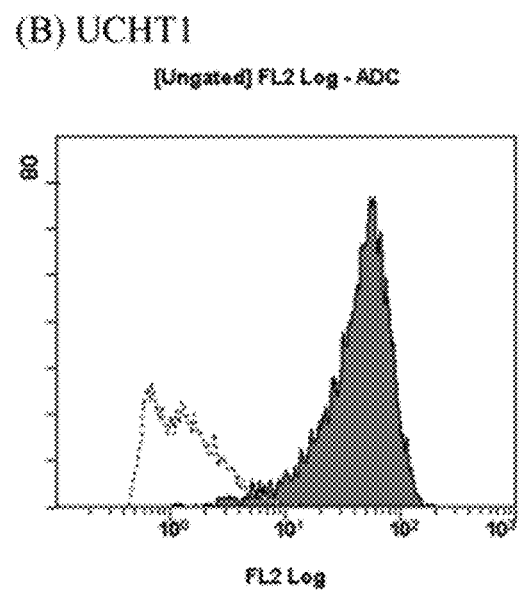
Figure 3C:
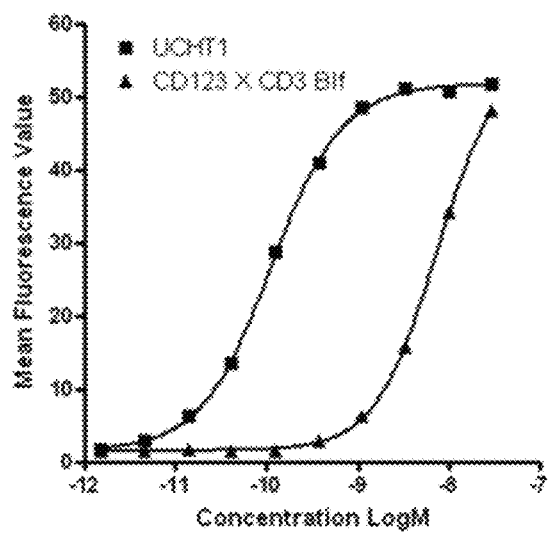

T Cell Binding Activities. Jurkat T cells were used to test CD123×CD3 BIf's abilities to recruit T cells. At 1 µg/ml, CD123×CD3 BIf already showed lower binding activities than the original UCHT1 antibody to Jurkat cells in flow cytometric analysis (FIGS. 3A and 3B). When serial titration of antibodies and the mean X-axis values were used to measure binding affinities, CD123×CD3 BIf showed a Kd at $10^{-8}$M, 2 orders higher than that of UCHT1 (FIG. 3C). This reduced T cell binding affinity would help to prevent non-specific T-cell activation.

BIf-Mediated T Cell Cytotoxicities. Since our BIf construct contains the Fc region of human IgG1 sequences, it is possible to be bound by Fc receptors on effector cells and activate ADCC. To focus only on T cell cytotoxicity, total T lymphocytes purified from healthy donors were used to test BIf activities. Two assays were conducted to evaluate BIf and effector cells efficacies. Target cell released lactose dehydrogenase (LDH) during cell lysis has been reported to test effector functions. The higher LDH activities represent the higher cytotoxicities. The inventors also used CFSE pre-labeled adherent cells as targets and compared the remaining fluorescent counts after treatments. The lower remaining fluorescent counts indicate stronger cellular cytotoxicities. These two methods showed comparable results in all tests.

Figures 4A, 4B:
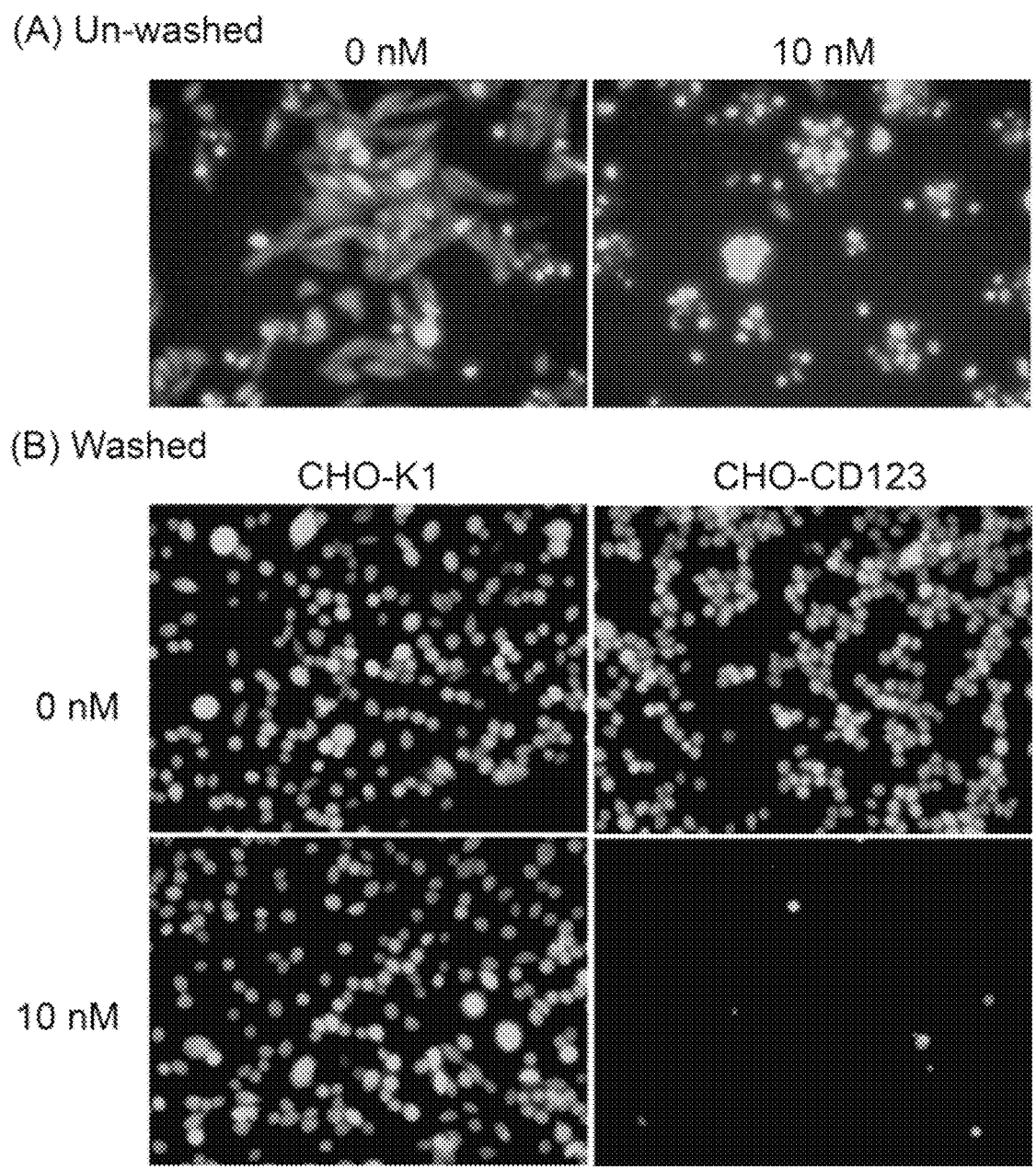
FIG. 4. Fluorescent images of CellTrace-labeled cells. $4 \times 10^4$ CFSE-labeled CHO-K1 or CHO-CD123 cells were seeded in each well of a 96-well black plate with glass bottom. (A) $4 \times 10^5$ purified T lymphocytes (E/T=10) were added into each well with (right) or without (left) 10 nM of CD123×CD3 BIf and incubate at 37° C., 5% $CO_2$ overnight. Fluorescent images were taken directly without wash. In the absence of BIf, majority of CHO-CD123 cells were remaining attached. Conversely, in the presence of BIf, most treated CHO-CD123 cells were detached from the plate. (B) Same as in (A) but each well was washed twice with PBS. The non-targeted CHO-K1 cells were not affected but most CHO-CD 123 cells were washed off.
Figures 5A, 5B:
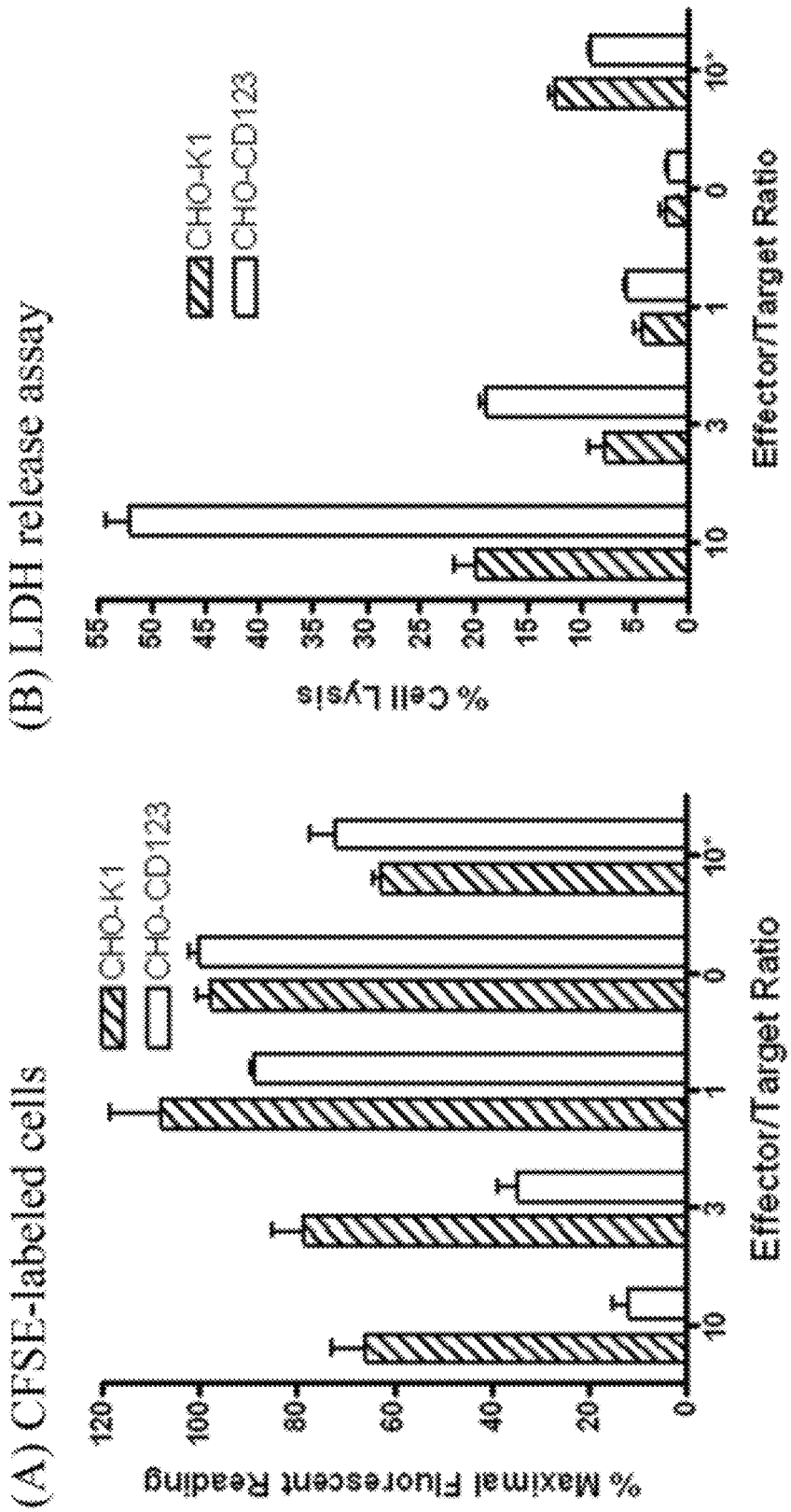
FIG. 5. CD123×CD3 BIf-mediated T cell cellular cytotoxicity assays. When 10 nM of CD123×CD3 BIf was used, cellular cytotoxicities at different E/T ratio were quantitively measured by (A) CFSE fluorescent counts of CHO-K1 (striped bars) and CHO-CD123 (open bars) cells; or (B) LDH released from CHO-K1 (striped bars) and CHO-CD123 (open bars) cells. Total fluorescent counts in non-treated cells; and LDH activities from Triton-lysed same number cells were defined as 100% in (A) and (B), respectively. 10*: E/T=10, but no BIf.
Figure 6:
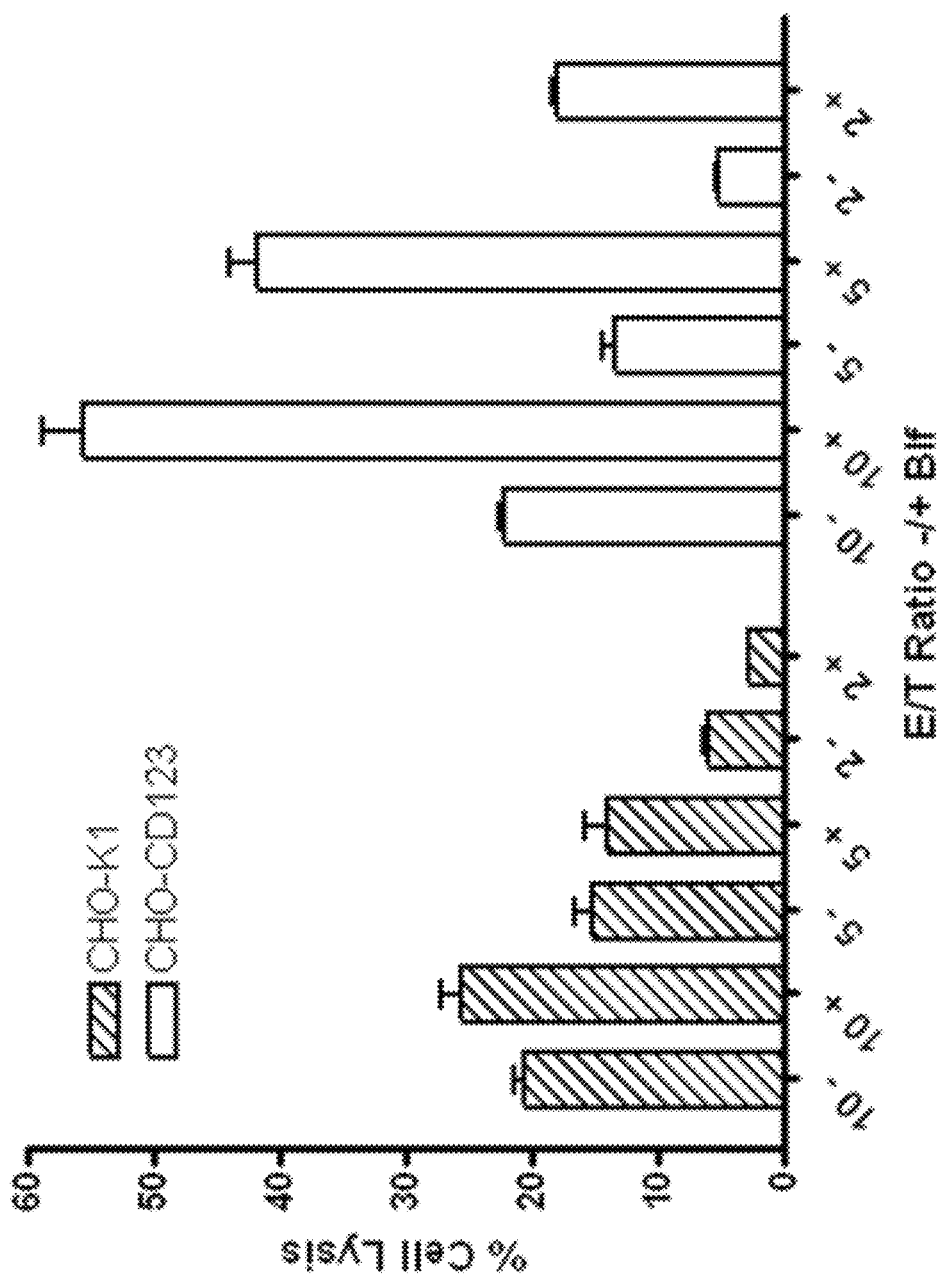
FIG. 6. The optimal E/T ratio. LDH release assays were used to define the optimal E/T ratio in the presence (+) or absence (−) of 10 nM CD123×CD3 BIf. CHO-K1 (striped bars) and CHO-CD123 (open bars) cells were used as non-targeted and targeted cells. Total LDH activities from Triton-lysed same number cells were defined as 100%.

To begin, 10 nM of BIf was used to test the optimal effector/target ratio (E/T). Initial tests showed that the efficacy reach plateau at an E/T ratio less than 10 (FIG. 4 and data not shown), and further titrations were done to refine the optimal E/T ratio. As shown in FIG. 5, the optimal E/T ratio is at between 3 and 10. The inventors found that, in the absence of BIf (FIGS. 5A and 5B, 10*), the T-cell alone had cell lysis activities (compare 0 and 10*). To focus on the BIf effect, reactions at even more narrowed E/T ratio ranges with or without BIf were compared. Indeed, the non-specific T cell killing effect is dose-dependent, and the additional 10 nM BIf dramatically enhanced the cytotoxic effects in CHO-CD123, but not in non-targeted CHO-K1 cells (FIG. 6). The target-specific cellular cytotoxicity can be seen at an E/T ratio as low as 2.

Figure 7:
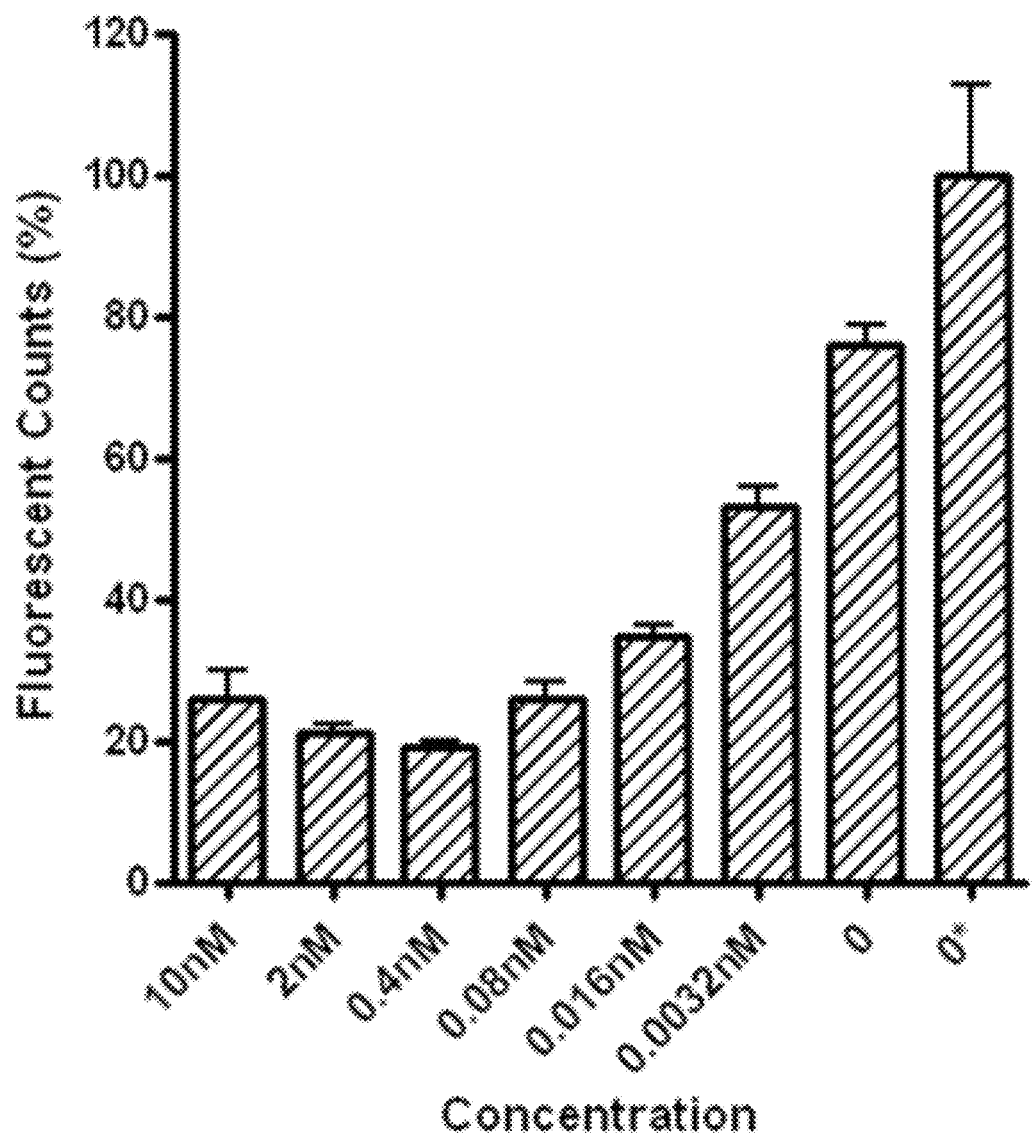
FIG. 7. CD123×CD3 BIf dose responses. When E/T was set at 5, different amounts of CD123×CD3 BIf were titrated into CFSE labeled CHO-CD123 cells. 0*: in the absence of both BIf and T cells and defined as 100%.

The E/T ratio was fixed at 5 to test BIf dose responses. As shown in FIG. 7, the effective dose to achieve 50% maximal cellular cytotoxicity is at ~$10^{-11}$ M, and the maximal activity can be reached at the concentration of $10^{-10}$ M. It is interesting to note that in repeated tests, BIf at higher than optimal concentrations produced less cytotoxic effects.

Figure 8:
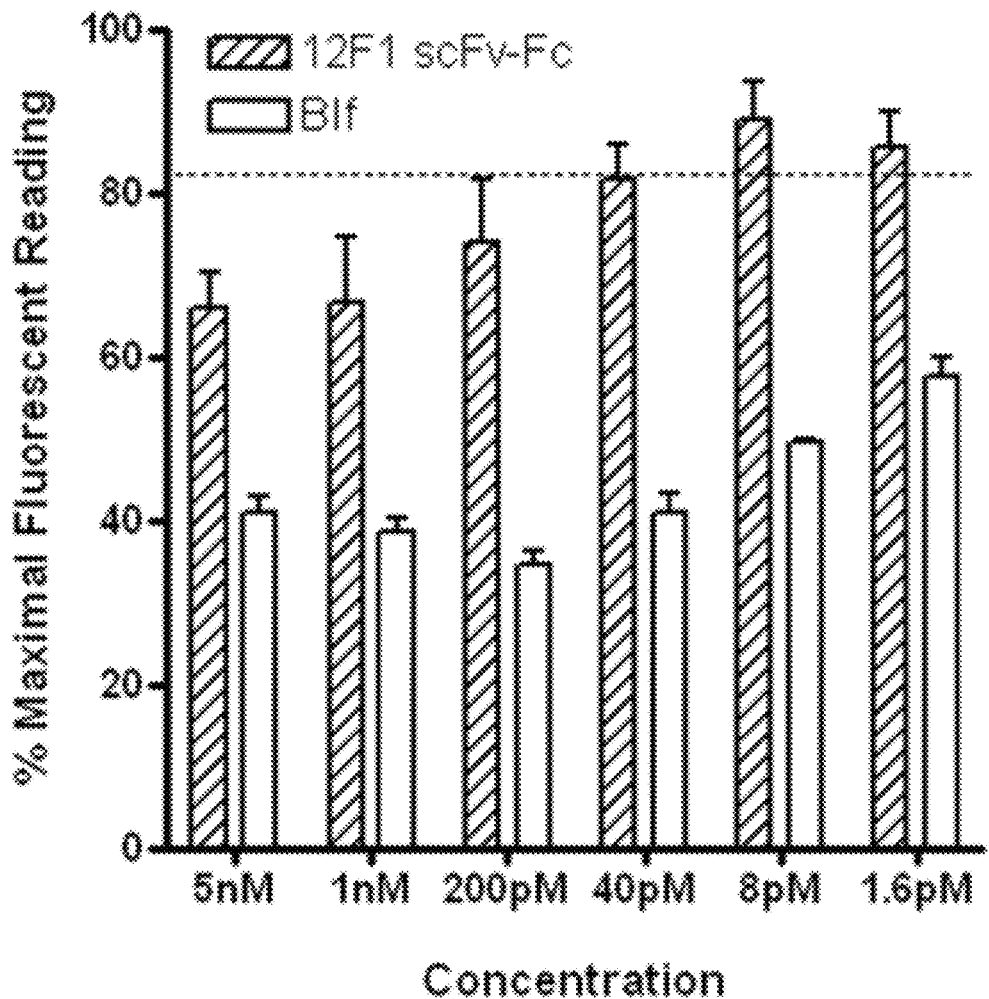
FIG. 8. ADCC versus T-cell cytotoxicities. $2 \times 10^5$ PBL were added into black 96-well glass bottom plate with $4 \times 10^4$ CFSE-labeled CHO-CD123 cells (E/T=5) and different concentrations of 12F1scFv-Fc (striped bars) or CD123×CD3 BIf (open bars) as indicated at X-axis. The total fluorescent counts from un-treated cells were set as 100%; and the dotted line indicated the activities of PBL in the absence of fusion proteins.

T Cell Cytotoxicity Versus ADCC. As mentioned earlier, the included human IgG1 Fc region in our BIf construct could also interact with other effector cells carrying Fc receptors and activate ADCC responses. To distinguish ADCC and T cell cytotoxicity, the non-adherent peripheral blood lymphocytes (PBL) were used as effector cells, and 12F1scFv-Fc was used as ADCC control. CFSE-labeled CHO-CD123 cells were treated with a serial titration of 12F1scFv-Fc or CD123×CD3 BIf and PBL at an E/T ratio of 5 for overnight. The remaining fluorescent counts after washes were measured by a plate reader. While 12F1scFv-Fc started to induce ADCC at ~200 pM and showed low cytotoxic effects at 5 nM, CD123×CD3 BIf showed stronger cytotoxic effects at low pM levels and reached a maximum at 200 pM (FIG. 8). The inventors concluded that ADCC might contribute to BIf's target cell killing activities, but in a very minor role.

Figure 9:
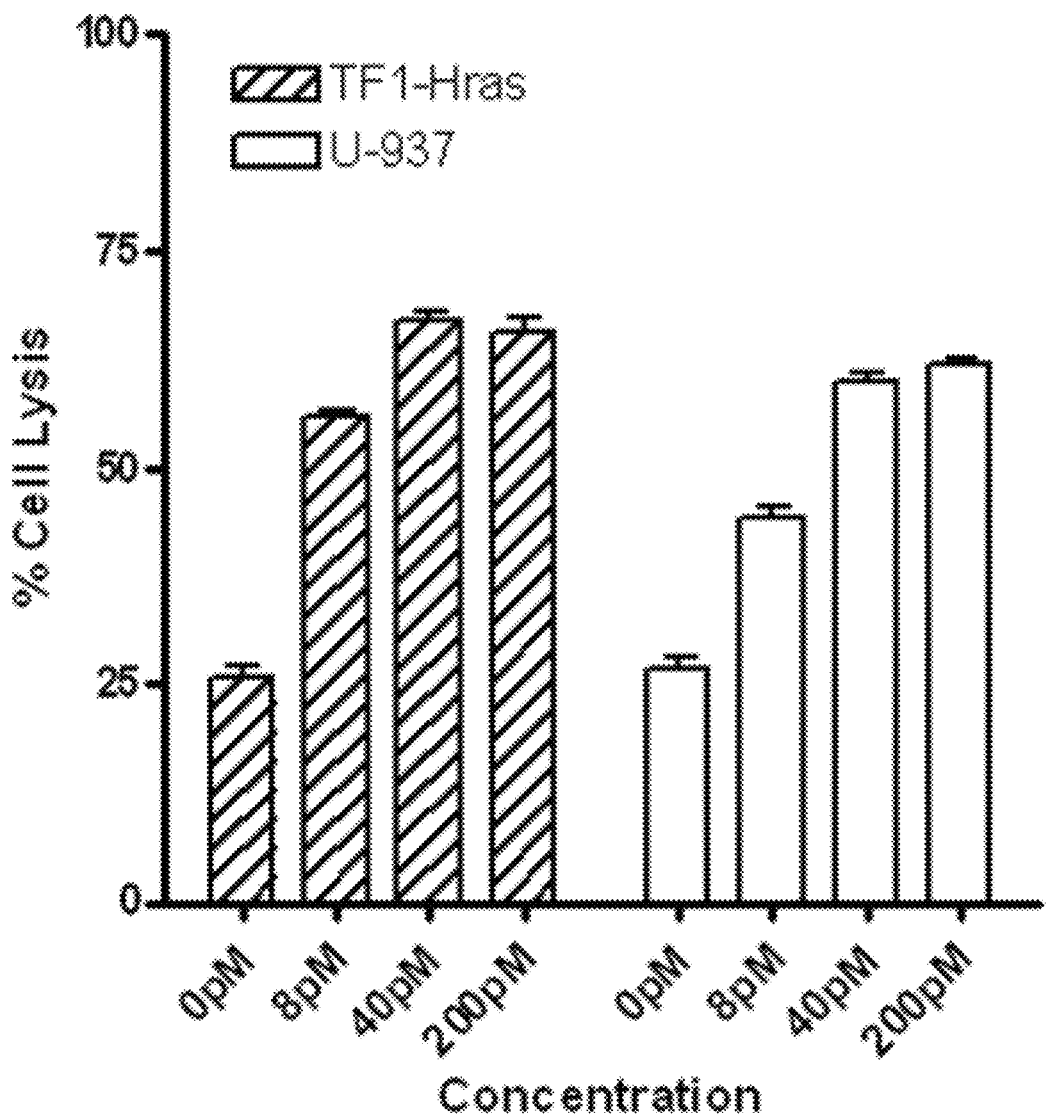
FIG. 9. Cytotoxic effects toward AML cell lines. AML cell lines TF1-Hras (striped bars) and U-937 (open bars) were treated with PBL at an E/T ratio of 5 and CD123×CD3 BIf at concentrations indicated on the X-axis. Total LDH activities from Triton-lysed same number cells were defined as 100%.

Cytotoxic Effects Toward AML Cell Lines. Established AML cell lines were used as target cells to test BIf efficacies. TF1 cells transfected with H-ras were used extensively in our previous studies targeting IL-3Rs and the estimated average CD123 copy number on these cells is less than 1,000. Compared to CHO-CD123 cells that have average 30,000 to 60,000 copies per cell, TF1/Hras is considered to be low on CD123 copy number. U-937 was also reported as a CD123+AML cell line with a lower number of cell surface CD123. These suspension cultured cells were tested in BIf-mediated T cell cytotoxicity assays using released LDH as an indicator. As shown in FIG. 9, TF1/Hras is sensitive to BIf at around the same concentration as CHO-CD123 and U-937 required slightly higher concentrations to reach the same efficacies. The inventors concluded that CD123×CD3 BIf carries the activities to bring CD123+AML cells and CD3+ cytotoxic T lymphocyte together to achieve target cell killing activities.

The invention claimed is:

1. A homodimer that specifically binds CD123 and CD3, wherein said homodimer comprises a polypeptide comprising a target binding domain that specifically binds CD123, an effector binding domain that specifically binds CD3, and an immunoglobulin constant region linker operatively coupling the target binding domain and the effector binding domain.

2. The homodimer of claim 1, wherein the target binding domain comprises SEQ ID NO:2.

3. The homodimer of claim 1, wherein the effector binding domain comprises SEQ ID NO:3.

4. The homodimer of claim 1, wherein the effector binding domain comprises hypervariable regions that are identical to the hypervariable regions of SEQ ID NO:3.

5. The homodimer of claim 1 wherein the immunoglobulin constant region is a human IgG constant region.

6. The homodimer of claim 5 wherein the human IgG constant region comprises SEQ ID NO:4.

7. A method for treating cancer comprising providing an effective amount of the homodimer of claim 1 to a cancer patient whose cancer cells express CD123.

8. A bispecific scFv immunofusion (BiF) polypeptide having an amino acid sequence of SEQ ID NO:1 and that specifically binds CD123 and CD3 cell surface proteins.

9. A method for treating cancer comprising providing an effective amount of the BiF polypeptide of claim 8 to a cancer patient whose cancer cells express CD123.

10. An anti-CD123 scFv-Fc fusion protein homodimer comprising a polypeptide that comprises the variable regions of SEQ ID NO:2, and an immunoglobulin constant region.

11. The anti-CD123 scFv-Fc fusion protein homodimer of claim 10 wherein the immunoglobulin constant region comprises SEQ ID NO:4.

12. An anti-CD123 scFv-Fc fusion protein homodimer comprising a polypeptide that comprises the variable regions of SEQ ID NO:2, and the hinge-CH2-CH3 segment of human IgG1.

* * * * *

(12) EX PARTE REEXAMINATION CERTIFICATE (11749th)
United States Patent
Liu et al.

(10) Number: US 9,745,381 C1
(45) Certificate Issued: Oct. 30, 2020

(54) BISPECIFIC SCFV IMMUNOFUSION (BIF)

(71) Applicant: Scott & White Healthcare, Temple, TX (US)

(72) Inventors: Jen-Sing Liu, Austin, TX (US); Shu-Ru Kuo, Temple, TX (US)

(73) Assignee: Aptevo Research and Development LLC

Reexamination Request:
No. 90/014,165, Jul. 13, 2018
No. 90/014,299, May 3, 2019

Reexamination Certificate for:
Patent No.: 9,745,381
Issued: Aug. 29, 2017
Appl. No.: 14/402,009
PCT Filed: May 18, 2013
PCT No.: PCT/US2013/041739
§ 371 (c)(1),
(2) Date: Nov. 18, 2014
PCT Pub. No.: WO2013/173820
PCT Pub. Date: Nov. 21, 2013

Related U.S. Application Data

(60) Provisional application No. 61/649,211, filed on May 18, 2012.

(51) Int. Cl.
 *C07K 16/28* (2006.01)
 *C07K 16/30* (2006.01)

(52) U.S. Cl.
 CPC .......... *C07K 16/30* (2013.01); *C07K 16/2809* (2013.01); *C07K 16/2896* (2013.01); *C07K 16/2866* (2013.01); *C07K 2317/31* (2013.01); *C07K 2317/52* (2013.01); *C07K 2317/56* (2013.01); *C07K 2317/622* (2013.01); *C07K 2317/64* (2013.01); *C07K 2317/732* (2013.01); *C07K 2317/92* (2013.01)

(58) Field of Classification Search
None
See application file for complete search history.

(56) References Cited

To view the complete listing of prior art documents cited during the proceedings for Reexamination Control Numbers 90/014,165 and 90/014,299, please refer to the USPTO's public Patent Application Information Retrieval (PAIR) system under the Display References tab.

*Primary Examiner* — Padmashri Ponnaluri

(57) ABSTRACT

Certain embodiments are directed to a bispecific immunoglobulin that is capable of binding cell surface molecules on a target cell, such as cancer cells, and cell surface molecules on immune effector cell, such as cytotoxic T lymphocytes, resulting in the targeted killing of target cells. In certain aspects a Bif is a polypeptide comprising a first target binding domain that specifically binds a cancer cell, a second effector binding domain that specifically binds an immunologic effector, and an immunoglobulin constant region linker operatively coupling the first and second binding domain.

EX PARTE
REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-2, 5-7 and 10-12 are cancelled.

Claims 3-4 and 8-9 were not reexamined.

\* \* \* \* \*

SEQUENCE LISTING

<160> NUMBER OF SEQ ID NOS: 19

<210> SEQ ID NO 1
<211> LENGTH: 726
<212> TYPE: PRT
<213> ORGANISM: Artificial Sequence
<220> FEATURE:
<223> OTHER INFORMATION: Synthetic peptide

<400> SEQUENCE: 1

Asp Ile Met Met Ser Gln Ser Pro Ser Ser Leu Ala Val Ser Val Gly
1               5                   10                  15

-continued

```
Glu Lys Phe Thr Met Thr Cys Lys Ser Ser Gln Ser Leu Phe Phe Gly
             20                  25                  30

Ser Thr Gln Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Ala
 65                  70                  75                  80

Ile Ser Ser Val Met Pro Glu Asp Leu Ala Val Tyr Cys Gln Gln
                 85                  90                  95

Tyr Tyr Asn Tyr Pro Trp Thr Phe Gly Gly Gly Thr Lys Leu Glu Ile
             100                 105                 110

Lys Gly Ser Thr Ser Gly Ser Gly Lys Pro Gly Ser Gly Glu Gly Ser
             115                 120                 125

Thr Lys Gly Val Gln Leu Gln Glu Ser Gly Pro Gly Leu Val Lys Pro
 130                 135                 140

Ser Gln Ser Leu Ser Leu Thr Cys Ser Val Thr Asp Tyr Ser Ile Thr
145                 150                 155                 160

Ser Gly Tyr Tyr Trp Asn Trp Ile Arg Gln Phe Pro Gly Asn Lys Leu
             165                 170                 175

Glu Trp Met Gly Tyr Ile Ser Tyr Asp Gly Ser Asn Asn Tyr Asn Pro
             180                 185                 190

Ser Leu Lys Asn Arg Ile Ser Ile Thr Arg Asp Thr Ser Lys Asn Gln
             195                 200                 205

Phe Phe Leu Lys Leu Ser Ser Val Thr Thr Glu Asp Thr Ala Thr Tyr
210                 215                 220

Tyr Cys Ser Arg Gly Glu Gly Phe Tyr Phe Asp Ser Trp Gly Gln Gly
225                 230                 235                 240

Thr Thr Leu Thr Val Ser Ser Ala Arg Ser Asp Lys Thr His Thr Cys
             245                 250                 255

Pro Pro Cys Pro Ala Pro Glu Leu Leu Gly Gly Pro Ser Val Phe Leu
             260                 265                 270

Phe Pro Pro Lys Pro Lys Asp Thr Leu Met Ile Ser Arg Thr Pro Glu
             275                 280                 285

Val Thr Cys Val Val Val Asp Val Ser His Glu Asp Pro Glu Val Lys
             290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
             325                 330                 335

Thr Val Leu His Gln Asp Trp Leu Asn Gly Lys Glu Tyr Lys Cys Lys
             340                 345                 350

Val Ser Asn Lys Ala Leu Pro Ala Pro Ile Glu Lys Thr Ile Ser Lys
             355                 360                 365

Ala Lys Gly Gln Pro Arg Glu Pro Gln Val Tyr Thr Leu Pro Pro Ser
 370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
             405                 410                 415

Pro Glu Asn Asn Tyr Lys Thr Thr Pro Pro Val Leu Asp Ser Asp Gly
             420                 425                 430
```

```
Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
        450                 455                 460

His Tyr Thr Gln Lys Ser Leu Ser Leu Ser Pro Gly Lys Pro Trp Asp
465                 470                 475                 480

Ile Gln Met Thr Gln Thr Thr Ser Ser Leu Ser Ala Ser Leu Gly Asp
                485                 490                 495

Arg Val Thr Ile Ser Cys Arg Ala Ser Gln Asp Ile Arg Asn Tyr Leu
                500                 505                 510

Asn Trp Tyr Gln Gln Lys Pro Asp Gly Thr Val Lys Leu Leu Ile Tyr
            515                 520                 525

Tyr Thr Ser Arg Leu His Ser Gly Val Pro Ser Lys Phe Ser Gly Ser
        530                 535                 540

Gly Ser Gly Thr Asp Tyr Ser Leu Thr Ile Ser Asn Leu Glu Gln Glu
545                 550                 555                 560

Asp Ile Ala Thr Tyr Phe Cys Gln Gln Gly Asn Thr Leu Pro Trp Thr
                565                 570                 575

Phe Ala Gly Gly Thr Lys Leu Glu Ile Lys Gly Ser Thr Ser Gly Ser
                580                 585                 590

Gly Lys Pro Gly Ser Gly Glu Gly Ser Thr Lys Gly Glu Val Gln Leu
            595                 600                 605

Gln Gln Ser Gly Pro Glu Leu Val Lys Pro Gly Ala Ser Met Lys Ile
        610                 615                 620

Ser Cys Lys Ala Ser Gly Tyr Ser Phe Thr Gly Tyr Thr Met Asn Trp
625                 630                 635                 640

Val Lys Gln Ser His Gly Lys Asn Leu Glu Trp Met Gly Leu Ile Asn
                645                 650                 655

Pro Tyr Lys Gly Val Ser Thr Tyr Asn Gln Lys Phe Lys Asp Lys Ala
            660                 665                 670

Thr Phe Thr Val Asp Lys Ser Ser Thr Ala Tyr Met Glu Leu Leu
        675                 680                 685

Ser Leu Thr Ser Glu Asp Ser Ala Val Tyr Tyr Cys Ala Arg Ser Gly
        690                 695                 700

Tyr Tyr Gly Asp Ser Asp Trp Tyr Phe Asp Val Trp Gly Ala Gly Thr
705                 710                 715                 720

Thr Val Thr Val Ser Ser
                725

<210> SEQ ID NO 2
<211> LENGTH: 250
<212> TYPE: PRT
<213> ORGANISM: Artificial Sequence
<220> FEATURE:
<223> OTHER INFORMATION: Synthetic peptide

<400> SEQUENCE: 2

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
                20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60
```

```
Pro Asp Arg Phe Thr Gly Ser Gly Ser Gly Thr Asp Phe Thr Leu Ala
 65                  70                  75                  80

Ile Ser Ser Val Met Pro Glu Asp Leu Ala Val Tyr Tyr Cys Gln Gln
                 85                  90                  95

Tyr Tyr Asn Tyr Pro Trp Thr Phe Gly Gly Gly Thr Lys Leu Glu Ile
            100                 105                 110

Lys Gly Ser Thr Ser Gly Ser Gly Lys Pro Gly Ser Gly Glu Gly Ser
        115                 120                 125

Thr Lys Gly Val Gln Leu Gln Glu Ser Gly Pro Gly Leu Val Lys Pro
130                 135                 140

Ser Gln Ser Leu Ser Leu Thr Cys Ser Val Thr Asp Tyr Ser Ile Thr
145                 150                 155                 160

Ser Gly Tyr Tyr Trp Asn Trp Ile Arg Gln Phe Pro Gly Asn Lys Leu
                165                 170                 175

Glu Trp Met Gly Tyr Ile Ser Tyr Asp Gly Ser Asn Asn Tyr Asn Pro
            180                 185                 190

Ser Leu Lys Asn Arg Ile Ser Ile Thr Arg Asp Thr Ser Lys Asn Gln
        195                 200                 205

Phe Phe Leu Lys Leu Ser Ser Val Thr Thr Glu Asp Thr Ala Thr Tyr
210                 215                 220

Tyr Cys Ser Arg Gly Glu Gly Phe Tyr Phe Asp Ser Trp Gly Gln Gly
225                 230                 235                 240

Thr Thr Leu Thr Val Ser Ser Ala Arg Ser
            245                 250

<210> SEQ ID NO 3
<211> LENGTH: 247
<212> TYPE: PRT
<213> ORGANISM: Artificial Sequence
<220> FEATURE:
<223> OTHER INFORMATION: Synthetic peptide

<400> SEQUENCE: 3

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Arg Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Arg Leu His Ser Gly Val Pro Ser Lys Phe Ser Gly
     50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Ala Gly Gly Thr Lys Leu Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Gln Gln Ser Gly Pro Glu Leu Val Lys Pro Gly Ala Ser Met Lys
130                 135                 140

Ile Ser Cys Lys Ala Ser Gly Tyr Ser Phe Thr Gly Tyr Thr Met Asn
145                 150                 155                 160

Trp Val Lys Gln Ser His Gly Lys Asn Leu Glu Trp Met Gly Leu Ile
                165                 170                 175
```

```
Asn Pro Tyr Lys Gly Val Ser Thr Tyr Asn Gln Lys Phe Lys Asp Lys
                180                 185                 190

Ala Thr Phe Thr Val Asp Lys Ser Ser Thr Ala Tyr Met Glu Leu
            195                 200                 205

Leu Ser Leu Thr Ser Glu Asp Ser Ala Val Tyr Tyr Cys Ala Arg Ser
        210                 215                 220

Gly Tyr Tyr Gly Asp Ser Asp Trp Tyr Phe Asp Val Trp Gly Ala Gly
225                 230                 235                 240

Thr Thr Val Thr Val Ser Ser
            245

<210> SEQ ID NO 4
<211> LENGTH: 229
<212> TYPE: PRT
<213> ORGANISM: Artificial Sequence
<220> FEATURE:
<223> OTHER INFORMATION: synthetic peptide

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Pro Trp
225

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
```

```
gatatcggac attatgatgt cacag                                          25
```

<210> SEQ ID NO 6
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 6

```
ttcaccgctt cccggttttc cggagccaga ggtgctacct ttgatttcca gtttggt     57
```

<210> SEQ ID NO 7
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 7

```
tccggaaaac cgggaagcgg tgaagggtcc accaagggtg tgcagcttca ggagtcg     57
```

<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 8

```
agatctggct gaggagactg tgagagt                                       27
```

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

```
Gly Ser Thr Ser Gly Ser Gly Lys Pro Gly Ser Gly Glu Gly Ser Thr
1               5                   10                  15

Lys Gly
```

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10

```
agatctggat caccatgg                                                 18
```

<210> SEQ ID NO 11
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 11

```
taactcgagg ctagc                                                    15
```

```
<210> SEQ ID NO 12
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 12
agatctgaca aaactcacac atgc                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
ccatggttta cccggagaca ggga                                              24

<210> SEQ ID NO 14
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 14

Asp Ile Val Met Thr Gln Thr Pro Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

Arg Ala

<210> SEQ ID NO 15
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 15

Gln Val Lys Leu Glu Glu Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Phe Gly Asp Ala Thr Tyr Asn Gln Lys Phe
    50                  55                  60

Lys Gly Lys Ala Thr Met Thr Val Asp Ser Ser Ser Thr Ala Tyr Met
```

```
                65                  70                  75                  80
Glu Leu Ala Arg Leu Thr Ser Glu Asp Ser Ala Ile Tyr Tyr Cys Ala
                85                  90                  95

Arg Glu Asp Tyr Val Pro Phe Ala Tyr Trp Gly Gln Gly Thr Leu Val
            100                 105                 110

Thr Val Ser Ala
        115

<210> SEQ ID NO 16
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 16

Trp Asp Ile Val Met Thr Gln Ser His Lys Phe Met Ser Thr Ser Val
1               5                   10                  15

Gly Asp Arg Val Ser Ile Ile Cys Lys Ala Ser Gln Asp Val Gly Thr
            20                  25                  30

Ala Val Asp Trp Tyr Gln Gln Lys Pro Gly Gln Ser Pro Lys Leu Leu
        35                  40                  45

Ile Tyr Trp Ala Ser Thr Arg His Thr Gly Val Pro Asp Arg Phe Thr
    50                  55                  60

Gly Ser Gly Ser Gly Thr Asp Phe Thr Leu Thr Ile Thr Asn Val Gln
65                  70                  75                  80

Ser Glu Asp Leu Ala Asp Tyr Phe Cys Gln Gln Tyr Asn Ser Tyr Pro
                85                  90                  95

Leu Thr Phe Gly Ala Gly Thr Met Leu Asp Leu Lys
            100                 105

<210> SEQ ID NO 17
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 17

Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110
```

```
Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 18

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Ser Ile Thr
                85                  90                  95

Phe Gly Gln Gly Thr Lys Leu Glu Ile Lys Arg
            100                 105

<210> SEQ ID NO 19
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Val Ala Asn Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Glu Gly Thr Met
            100                 105                 110

Val Thr Val Ser Ser
        115
```